(12) United States Patent
Bressler et al.

(10) Patent No.: US 8,896,682 B2
(45) Date of Patent: Nov. 25, 2014

(54) SYSTEM AND METHOD FOR AUTOMATED DETECTION OF AGE RELATED MACULAR DEGENERATION AND OTHER RETINAL ABNORMALITIES

(75) Inventors: Neil Bressler, Owings Mills, MD (US); Philippe Martin Burlina, North Bethesda, MD (US); David Eric Freund, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 359 days.

(21) Appl. No.: 13/139,499

(22) PCT Filed: Dec. 22, 2009

(86) PCT No.: PCT/US2009/069223
§ 371 (c)(1),
(2), (4) Date: Jun. 13, 2011

(87) PCT Pub. No.: WO2010/071898
PCT Pub. Date: Jun. 24, 2010

(65) Prior Publication Data
US 2011/0242306 A1    Oct. 6, 2011

Related U.S. Application Data

(60) Provisional application No. 61/139,053, filed on Dec. 19, 2008.

(51) Int. Cl.
*G06T 5/00* (2006.01)
*A61B 3/12* (2006.01)

(52) U.S. Cl.
CPC ...................................... *A61B 3/12* (2013.01)
USPC ........................................................... 348/78

(58) Field of Classification Search
CPC ................... G06T 2207/30041; G06T 2200/00
USPC ............................................................ 348/78
See application file for complete search history.

(56) References Cited

U.S. PATENT DOCUMENTS

| | | | |
|---|---|---|---|
| 6,970,576 B1 * | 11/2005 | Tilsley .......................... | 382/103 |
| 2001/0056237 A1 * | 12/2001 | Cane et al. ..................... | 600/475 |
| 2007/0258630 A1 | 11/2007 | Tobin et al. | |
| 2007/0287932 A1 | 12/2007 | Huang et al. | |
| 2008/0309881 A1 | 12/2008 | Huang et al. | |
| 2010/0238404 A1 * | 9/2010 | Newman et al. ............... | 351/208 |
| 2011/0157550 A1 * | 6/2011 | Chen et al. ..................... | 351/206 |

OTHER PUBLICATIONS

International Search Report and Written Opinion of PCT/US2009/069223.

(Continued)

*Primary Examiner* — Sath V Perungavoor
*Assistant Examiner* — Jeffery Williams
(74) *Attorney, Agent, or Firm* — Venable LLP; Henry J. Daley; Todd R. Farnsworth

(57) ABSTRACT

A system and method for automated detection of age related macular degeneration and other retinal abnormalities which may have a retinal scanner capable of obtaining retinal data from a subject. The retinal scanner may be coupled to a central processing unit (CPU) which may have memory storing CPU-executable instructions which may detect retinal abnormalities. When the CPU receives retinal data from the retinal scanner, the system may perform CPU-executable instructions for detecting retinal abnormalities. The system may analyze the retinal data to determine one or more healthy areas and, based on the analyzed healthy area, the system may detect abnormalities in the retinal data.

48 Claims, 13 Drawing Sheets

(56) References Cited

OTHER PUBLICATIONS

Banerjee, et al., A Support Vector Method for; Anomaly Detection in Hyperspectral Imagery, IEEE Trans. Geoscience Remote Sensing, vol. 8(44), pp. 2282-2291 (2006).

Brandon, et al., Drusen Detection in a Retinal Image Using Multilevel analysis, MICCAI 2003, LNCS 2878, ed. Ellis, et al., pp. 618-625, Springer-Verlag (2003).

Chanwimaluang, et al., An efficient blood vessel detection algorithm for retinal images using local entropy thresholding, in Circuits and Systems, ISCAS '03, vol. 5, p. V-21-V-24. May 25-28, 2003.

Freund, et al., Characterization of Spatial Ordering of Corneal Stroma Fibrils, Johns Hopkins University Applied Physics Laboratory & Computer Science Department (2008).

Hoover, et al., Locating the Optic Nerve in a Retinal Image Using the Fuzzy Convergence of the Blood Vessels, IEEE Transactions on Medical Imaging 22, pp. 951-958; (2003).

Jelnek, et al., Automated Segmentation of Retinal Blood Vessels and Identification of Proliferative Diabetic Retinopathy, J. Opt. Soc. Am 24(5) pp. 1445-1456 (2007).

Salem, et al., Segmentation of retinal blood vessels using scale-space features and; K-nearest neighbor classifier, in Proc. 31st International Conference on Acoustics, Speech, and Signal Processing—ICASSP '06, May 14-19, 2006, Toulouse, France.

Scholkopf, et al., Estimating the Support of a High-Dimensional Distribution, Neural Computation 13 (2001), pp. 1443-1471.

Tax, et al. Data Domain Description using Support Vectors, ESANN'1999 proceedings—European Symposium on Artificial Neural Networks Bruges (Belgium), Apr. 21-23, 1999, D.-Facto public., ISBN 2600049-9-X, pp. 251-256.

Tax, et al., Support Vector Data Description Applied to Machine Vibration Analysis, Pattern Recognition Group, Dept. of Applied Physics, Faculty of Applied Sciences, Delft University of Technology Lorentzweg 1, 2628 CJ Delft, The Netherlands (no date).

Tax, et al., Support Vector Data Description Machine Learning, 54, 45-66 (2004).

Tax, et al., Support Vector Domain Description, Pattern Recognition Letters 20 (1999), pp. 1191-1199.

Weston, et al., "Support Vector Density Estimation," 1999, pp. 1-15.

\* cited by examiner

SYSTEM AND METHOD FOR AUTOMATED DETECTION OF AGE RELATED MACULAR DEGENERATION AND OTHER RETINAL ABNORMALITIES

CROSS-REFERENCE TO RELATED APPLICATION

This application claims priority to U.S. Provisional Application No. 61/139,053 filed Dec. 19, 2008, the entire content of which is hereby incorporated by reference, and is a U.S. national stage application under 35 U.S.C. §371 of PCT/US2009/069223, filed Dec. 22, 2009, the entire contents of which are incorporated herein by reference.

BACKGROUND

1. Field of Invention

The current invention relates to automated systems utilizing detection methods, and more particularly to an automated system operable to detect abnormalities of the eye.

2. Discussion of Related Art

The contents of all references, including articles, published patent applications and patents referred to anywhere in this specification are hereby incorporated by reference.

Age-related macular degeneration (AMD) is a disease of the retina that occurs mainly within the population over 50 and is the leading cause of blindness in this age group. Additional detail on the eye can be found in Hogan, et al., *Histology of the Human Eye*, W. B. Sanders, Philadelphia 1971. AMD has two manifestations, dry and wet (non-neovascular and neovascular). The dry form is the most prevalent and found in about 80% of the cases and can be further divided into an intermediate stage (the most prevalent dry form) and an advanced dry stage (atrophy of the retina, usually causing vision loss when involving the center of the retina). The intermediate stage of AMD is not accompanied by symptoms of vision loss. However, a defining asymptomatic sign indicating the onset of AMD is the presence of small accumulations of extracellular material in the retina called drusen. Drusen were first described in Donders, *Beitrage zur pathologischen Anatomic des Auges*. Archiv Für Ophthalmologic 1854, 1:106-18. Drusen form typically in the macula (the center of the retina) and represent a thickening of Bruch's membrane, just external to the outer layers of the retina and just internal to the vascular choroid of the eye. Small drusen are not uncommon at age 40 or 50 but large drusen are typically indicative of AMD. The mechanism for the formation of drusen and the way they lead to vision loss from atrophy of the wet form of AMD is not completely understood but one explanation is that their presence interferes with the supply of nutrients and oxygen to rods and cones.

The wet form of AMD, also considered an advanced stage of AMD because it typically leads to vision loss, is always preceded by drusen (the intermediate stage of AMD), although not necessarily by atrophy (the dry form of AMD and considered an advanced dry form when involving the center of the retina). The greater the area of drusen present in an eye, the greater chance the eye will progress to the advanced stage of AMD (either the dry atrophic form or the wet form or both). The wet form is manifested by the abnormal development of fragile blood vessels which often leak fluid or blood into or under the retina and are accompanied by ingrowth of scar tissue. It is the dysfunction of the retina from blood and fluid leaking from these vessels in the macula, along with loss of retina from atrophy or ingrowth of scar that eventually affects central vision needed for reading or driving, usually leaving peripheral vision intact. This is particularly significant since high resolution foveal vision is essential for basic occulomotor tasks such as fixation and saccading and to higher level vision tasks such as face recognition. Unfortunately, about 50% of people who develop the wet form in one eye will develop the wet form in the other eye within 5 years, so that wet AMD frequently leads to functional blindness. The prevalence of drusen is so common (approximately 8,000,000 people in the U.S. over the age of 50 with at least one eye having the intermediate stage of AMD), and the incidence of the wet form among those with the intermediate stage of AMD is so frequent (approximately 150,000 individuals each year among those with the intermediate stage) that AMD, left untreated, is the leading cause of blindness in people over the age of 50 in the United States and throughout much of the world. Wet AMD has several treatments: recently several anti-vascular endothelial growth factor (VEGF) therapy drugs have been FDA approved for injection into the eye to block the development of these vessels; use of at least one of these (ranibizumab), if applied before substantial loss has occurred, can reduce the incidence of legal blindness by about 75%.

While the intermediate stage of AMD is asymptomatic until atrophy affects the central macula or until the wet form develops, the advanced stage (the central atrophic dry form or the wet form) can cause severe vision loss and is expected to affect up to 3 million individuals in the US by 2020. The anti-VEGF therapies can prevent blindness in most cases provided the disease is detected and treated when progressing from the asymptomatic intermediate stage to the wet stage. It is essential to initiate these therapies before substantial vision loss has occurred so as to avoid functional blindness. This strategy requires an individual to know that he or she has the usually asymptomatic intermediate stage of AMD so that periodic self-monitoring and professional monitoring can occur to detect the onset of the wet stage, and so that these individuals will be educated as to how and where to seek prompt treatment if the wet form of AMD develops. In addition, there is some evidence to suggest that taking a dietary supplement such as that used in a government-sponsored study can reduce the risk of progression to the advanced stage in individuals who have the intermediate stage. Currently, detection methods such as ophthalmoscopy and clinical evaluation of fundus photographs by skilled specialists still remain the gold standard, but involve a completely manual and time consuming diagnostic workflow.

To perform a fundus examination it may be necessary to use an instrument to view and photograph the fundus of a patient's eye. For example, one such instrument in wide use is a fundus camera. FIG. 1 is an example of a conventional fundus camera 100. The fundus camera 100 is one example of an optical system to observe the fundus 102 of a subject's eye 104. The fundus camera 100 has an illumination path 106 and a viewing path 108. A constant illumination may be provided by an incandescence light bulb 110, for example. A brighter flash illumination may be provided by flash bulb 112 for use in conjunction with film-based cameras. Furthermore, the viewing path 108 may be split into a path for direct viewing 114 by a user and a path 116 to a camera 118 for photographing an image of the fundus 102 of the subject's eye 104. The beam splitter 120 may be replaced with a movable mirror 122 in some fundus cameras. The commercial fundus camera 100 is shown as an example and not meant to limit the scope of the current invention.

With the large baby-boom generation moving into its senior years, there is a real possibility that the relatively limited supply of clinicians may be unable to administer the necessary fundus examinations that are required for detection in a timely manner. Because of this, there is an important need for developing automated tools that can detect the intermediate stage AMD accurately and as a result allow for early education, intervention, and treatment of the wet form.

Furthermore, there is a need for automated algorithms that assist in subsequent tracking of the disease progression, which could help clinicians perform longitudinal studies and assess the effectiveness of various therapies aimed at reducing the development of progression of the intermediate stage.

SUMMARY

An embodiment for a system for automated detection of age related macular degeneration and other retinal abnormalities may include a retinal scanner which is capable of obtaining retinal data. The retinal scanner may be coupled to a central processing unit (CPU) having memory storing CPU-executable instructions for detecting retinal abnormalities. In response to receiving retinal data according to the CPU-executable instructions for detecting retinal abnormalities, the CPU may analyze the retinal data to determine a healthy area and may detect an abnormality in the retinal data based on the determined healthy area.

According to another embodiment, a method for automated detection of retinal abnormalities includes receiving retinal data from a retinal scanner coupled to a computer, characterizing a healthy area of the retina from the retinal data using the computer, and determining an area of abnormality in the retinal data that deviates from the characterized healthy area using the computer.

In yet another embodiment, a computer readable medium storing executable instructions for execution by a computer having memory, the medium stores instructions for: receiving retinal data from a retinal scanner coupled to the computer, characterizing a healthy area of the retina from the retinal data, and determining an area of abnormality in the retinal data that deviates from the characterized healthy area.

BRIEF DESCRIPTION OF THE DRAWINGS

The invention may be better understood by reading the following detailed description with reference to the accompanying figures, in which.

DETAILED DESCRIPTION

Figure 1:
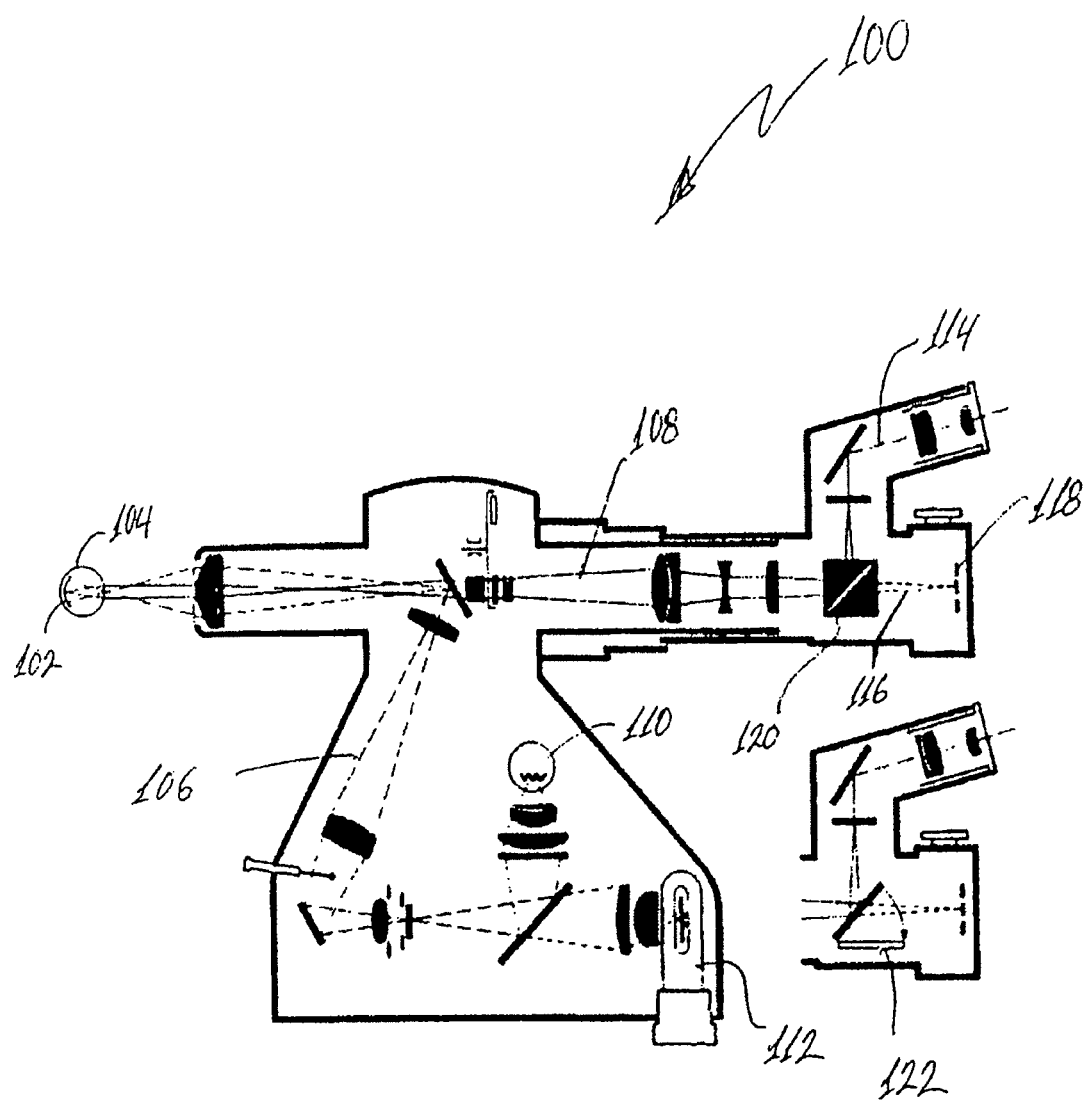
FIG. 1 is a schematic illustration of a conventional fundus imager.

AMD detection is usually conducted by clinicians using fundus examination and less commonly by obtaining a fundus photograph which subsequently is evaluated by an expert in fundus photograph interpretation. Medical resources to accomplish this manually are relatively scarce when compared to the size of the population at risk. One possible solution may be an agile fundus imaging-based detection system of early or intermediate stage AMD that may be deployed in a clinical setting or at a walk-in clinic which may use self-administered, non-mydriatic images. Images may be automatically processed using image analysis software that may provide robust detection. Suspect cases may be referred to a physician for further examination and monitoring.

In describing embodiments of the present invention illustrated in the drawings, specific terminology is employed for the sake of clarity. However, the invention is not intended to be limited to the specific terminology so selected. It is to be understood that each specific element includes all technical equivalents which operate in a similar manner to accomplish a similar purpose.

Figure 2:
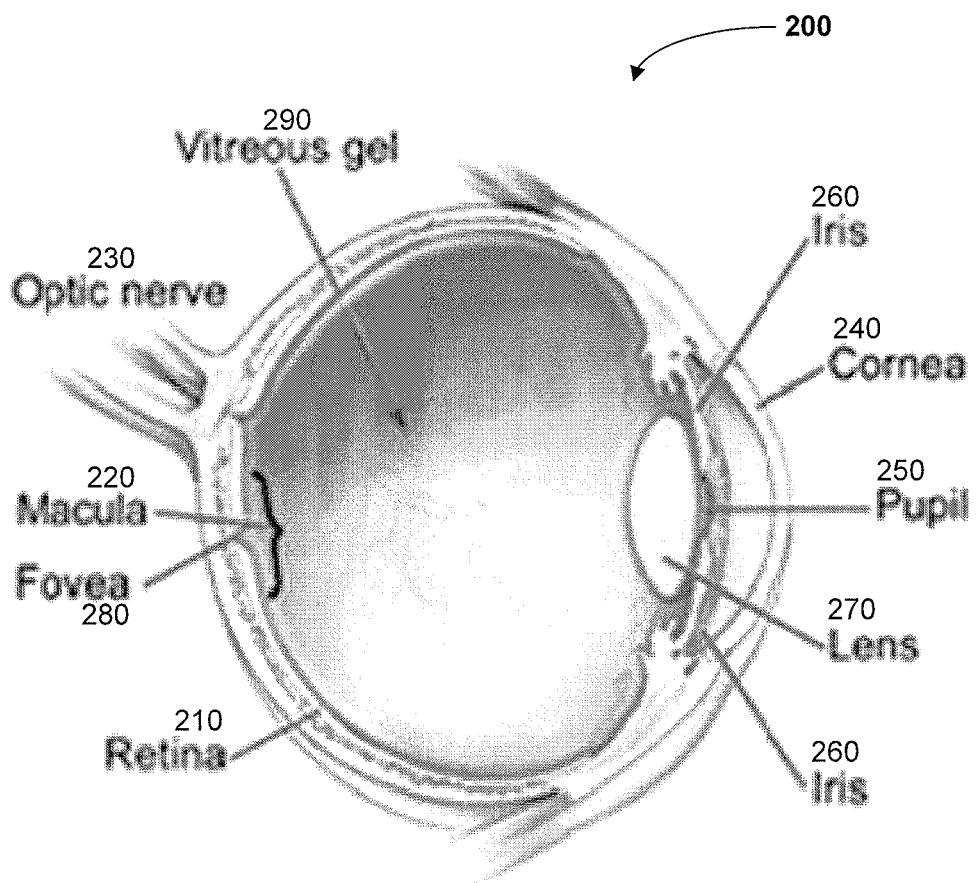
FIG. 2 is a cross sectional sketch of the human eye.

FIG. 2 is a cross sectional sketch of a typical human eye 200. The sketch depicts the retina 210, the macula 220, the optic nerve 230, the cornea 240, the pupil 250, the iris 260, the lens 270, the fovea 280, and vitreous gel 290.

Figure 3A:
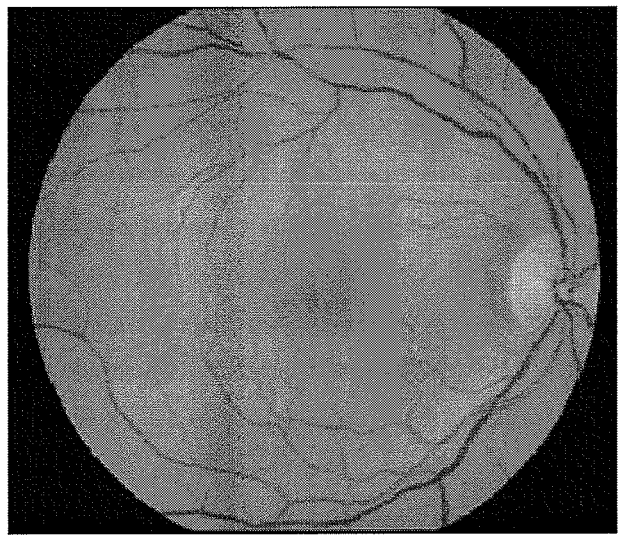
FIGS. 3A and 3B show a sample fundus image of (3A) a normal healthy human retina and (3B) a retina with age related macular degeneration.
Figure 3B:
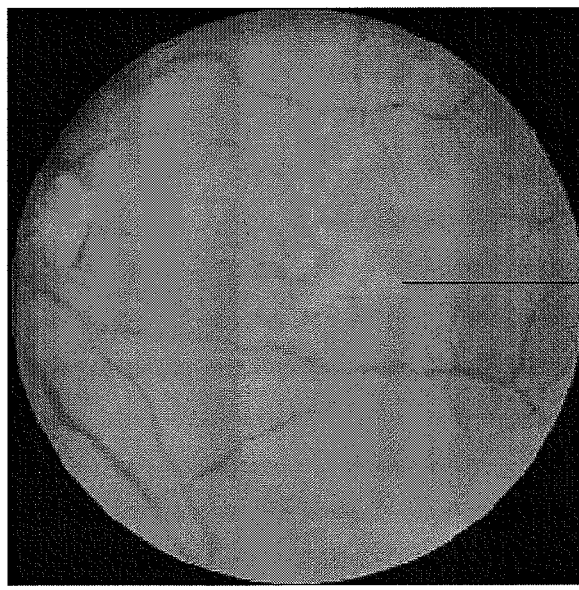

FIG. 3A and FIG. 3B (collectively 300) show, respectively, fundus images of a normal healthy retina and a retina of a patient suffering from the dry form of AMD. The normal eye FIG. 3A does not have any visible signs of drusen. While in FIG. 3B drusen appears as item 310.

A common theme echoed in prior work is the difficulty in detecting and locating drusen 310. One reason is that aspects of drusen 310, for example, shape, color, texture, extent, etc., may vary substantially from one individual to another. Because of the variance in drusen 310 between individuals, no currently existing classifier can encompass all possible embodiments of a druse. What may be a more practical approach may be to detect anomalies in each individual. Anomaly detection may be accomplished through a one-class classifier that may describe the 'normal' aspect of the background of the retina for healthy individuals and may detect regions of interest in retina images where the background may appear to deviate statistically from the 'normal' background. One possible difficulty in anomaly detection based on a parametric statistical model may be the selection of the probability density function (PDF). Often the choice of a default PDF may not model accurately the underlying data. In other situations there may not be enough data to describe all possible variations of the appearance of healthy tissue so as to test for the validity of the PDF model and estimate its parameters. These situations may lead to poor specificity (high false alarm rate) and sensitivity (low detection probability). Instead, what may be used is a non-parametric approach, such as, but not limited to, Support Vector Data Description (SVDD), which may find the optimal region of support in feature space of the features representing healthy retinal tissue.

One challenge in drusen 310 detection may occur when the eye 200 is affected by a condition such as cataract, in which case the fundus image 300 may appear blurred (not shown). Another problem may be that there is a wide variation in the size of the drusen and there may be no canonical orientation. These issues may be addressed through the use of a multi-scale texture-based analysis approach based on, for example, wavelet filtering, which may capture the characteristics of the image at different scales and different orientations.

Pre-Processing

Pre-processing, in one embodiment of this invention, is performed as follows: Although drusen 310 may appear as yellow spots against a red/orange background, much of the drusen 310 information may lie in the difference in intensity contrast which may be derived from the monochromatic image which may prompt the use of the green band. The image may also be subject to an intensity based equalization algorithm. See also, Brandon, et al., *Drusen Detection in a Retinal Image Using Multi-level analysis*, MICCAI 2003, LNCS 2878, ed. Ellis, et al., pp. 618-625, Springer-Verlag (2003); and Jelnek, et al., *Automated Segmentation of Retinal Blood Vessels and Identification of Proliferative Diabetic Retinopathy*, J. Opt. Soc. Am 24(5) pp. 1445-1456 (2007).

Texture Analysis

Figure 13:
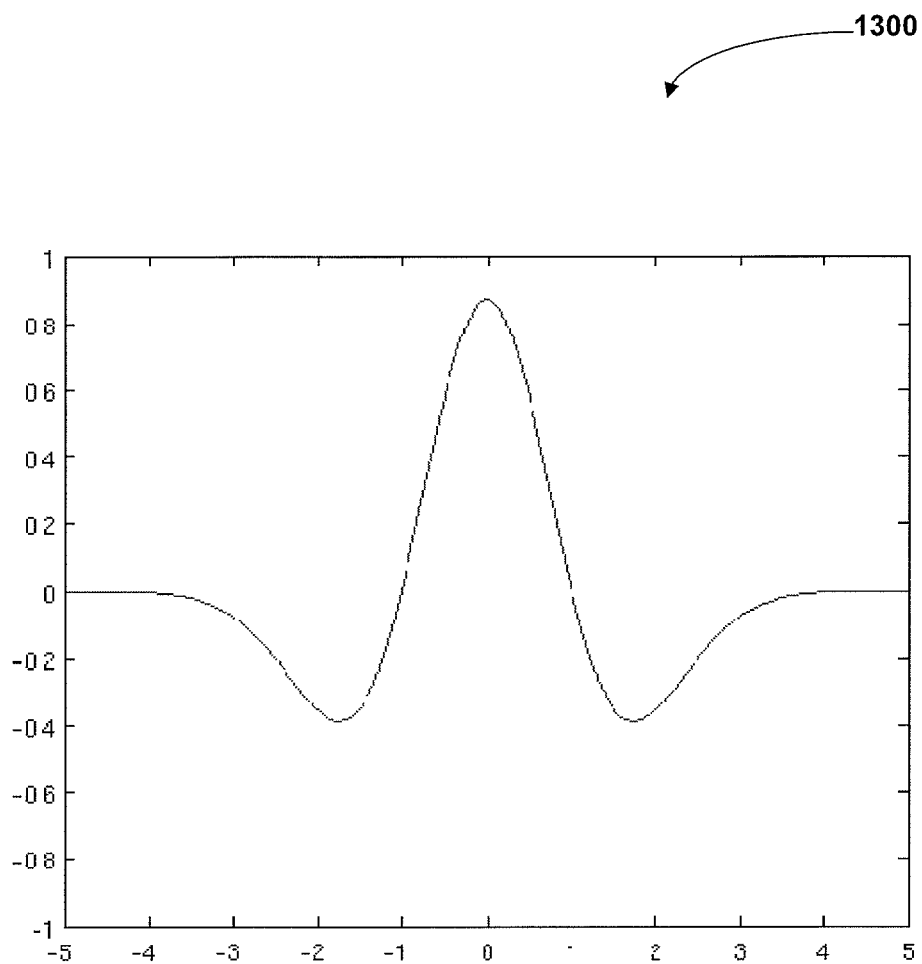
FIG. 13 depicts a Mexican hat wavelet created on MATLAB (v. 7.6.0).

Texture analysis, used in one embodiment of this invention, is performed using wavelets and is described as follows: After intensity equalization, a feature vector composed of the response of the image to filtering at different scales and orientations may be computed. For example, in one embodiment, the Mexican hat wavelet, also known as the Ricker wavelet (FIG. 13 depicts an illustrative graph of a sample Mexican hat wavelet), may be used, for example, to derive a set of feature values for each pixel in the image. The Mexican hat wavelet is proportional to the second derivative of the Gaussian probability density function and it is given by:

$$\psi_{mxxhat}(x) = \frac{2}{\pi^{\frac{1}{4}}\sqrt{3}}(1-x^2)\exp\left[\frac{-x^2}{2}\right].$$

A discretized approximation to the above equation could be used to perform, for example, four one dimensional (1D) wavelet convolutions about each pixel in the intensity equalized image. Convolutions along the horizontal, vertical, diagonal, and backward diagonal directions may be used. Each of the four 1D responses may be computed by convolving a 1D slice of the intensity equalized image with the Mexican hat wavelet, for example, such that:

$$I_{meshot}(r,c) = \psi_{meshot} * I_{eq}(r,c),$$

where * denotes 1D convolution. A value equal to the product of the four corresponding 1D convolutions evaluated at the center of the resulting 1D signal may be assigned to each pixel. This procedure may be performed for ten different wavelet dilations (i.e., convolution length) ranging from, for example, 10 to 100 in steps of 10. In general, each wavelet dilation may result in a different value being assigned to any given pixel. Thus each pixel may have a ten dimensional vector associated with it corresponding to the ten sets of convolutions. This procedure may be performed using the Gabor, Daubechies, Haar, or other wavelets. In addition, one could use two dimensional wavelet analysis to perform texture analysis and the creation of a feature vector.

Anomaly Detection

A method derived from Support Vector Machine called Support Vector Data Description (SVDD) may be used for anomaly detection. SVDD is further described in Tax, et al. *Data Domain Description using Support Vectors*, ESANN'1999 proceedings—European Symposium on Artificial Neural Networks Bruges (Belgium), 21-23 Apr. 1999, D-Facto public., ISBN 2-600049-9-X, pp. 251-256; Tax, et al., *Support Vector Data Description Applied to Machine Vibration Analysis*, Pattern Recognition Group, Dept. of Applied Physics, Faculty of Applied Sciences, Delft University of Technology Lorentzweg 1, 2628 C J Delft, The Netherlands (no date); Tax, et al., *Support Vector Data Description, Pattern Recognition Letters* 20 (1999), pp. 1191-1199; Tax, et al., *Support Vector Data Description Machine Learning*, 54, 45-66 (2004); Freund, et al., *Characterization of Spatial Ordering of Corneal Stroma Fibrils*, Johns Hopkins University Applied Physics Laboratory & Computer Science Department (2008); all of which are hereby incorporated by reference.

SVDD solves a constrained optimization problem to find the smallest D-dimensional sphere centered on a and of radius R enclosing the entire training set of vectors T={$x_i \in R^D$, i=1, 2, . . . M}. These vectors may have been formed from the multiscale feature responses and may have been derived as described above.

This constrained optimization problem may be solved by introducing slack variables and then defining the functional:

$$F(R,\xi) = R^2 + \kappa \sum_{i=1}^{M} \xi_i.$$

where $\kappa$ is a nonnegative constant. One may minimize $F(R,\xi)$ subject to the constraints $\xi_i \geq 0$ and $\|x_i-a\|^2 \leq R^2+\xi_i$ for i=1, 2, . . . M.

Using Lagrange multipliers then yields the following Lagrangian function:

$$L(R, a, \xi; \alpha, \gamma) = R^2 + \kappa \sum_i \xi_i - \sum_i \alpha_i[R^2 + \xi_i - \|x_i - a\|^2] - \sum_i \gamma_i \xi_i$$

where $\alpha_i$ and $\gamma_i$ are the Lagrange multipliers. Minimizing $L(R, a, \xi; \alpha, \gamma)$ with respect to R and a, gives:

$$\sum_i \alpha_i = 1, a = \sum_i \alpha_i x_i, \text{ and } \alpha_i + \gamma_i = \kappa.$$

which in turn leads to $$L(R, a, \xi; \alpha, \gamma) \to W(\alpha) \equiv \sum_i \alpha_i \langle x_i, x_i \rangle - \sum_{i,j} \alpha_i, \alpha_j \langle x_i, x_j \rangle$$

where $\langle x_i, x_j \rangle$ is an inner product in $R^D$. Finally, maximizing W(.) with respect to the $$\sum_i \alpha_i = 1$$

$\alpha_i$'s subject to the constraints and $0 \leq \alpha_i \leq \kappa$ yields the optimal values for the $\alpha_i$. In one solution only a small subset of the $\alpha_i$ may be nonzero. The training vectors associated with the nonzero values of $\alpha_i$ may be called support vectors and the support vectors lie on the optimal hypersphere's boundary.

The SVDD test statistic may be given by the squared distance to this boundary $$\|x - a\|^2 = \langle x, x \rangle - 2\sum_i \alpha_i \langle x, x_i \rangle + \sum_{i,j} \alpha_i \alpha_j \langle x_i, x_j \rangle.$$

The previous equation may specify a 'test statistic' which may further be generalized to allow for non-spherical support regions by using a non-linear kernel function, K(x,y), to replace the linear inner-product. That is, if K(x,y) is a continuous, symmetric, and positive semi-definite function in L2, then a mapping, $\Phi(x)$, exists that implicitly maps the training data points from $R^D$ into a higher (possibly infinite) dimensional induced feature space such that K(x,y) represents an inner product in this new induced feature space.

The test statistic may then be rewritten in terms of the kernel, K(x,y), as:

$$ST(x) \equiv \|\Phi(x) - c\|^2 = K(x, x) - 2\sum_i \alpha_i K(x, x_i) + \sum_{i,j} \alpha_i \alpha_j K(x_i, x_j)$$

where c is the center of the minimal hypersphere in the induced feature space:

$$c = \sum_i \alpha_i \Phi(x_i).$$

Although the SVDD $K(x,y)=\langle\Phi(x), \Phi(y)\rangle$ function may be a sphere in the induced feature space, in the original feature space it may model the support of an arbitrary non-Gaussian, multi-modal function that may more accurately capture the distribution of the data.

A Gaussian radial basis function (RBF) may be used for the kernel function which may lead to the simplified statistic:

$$ST(x) = C - 2\sum_i \alpha_i K(x, x_i)$$

with C being a constant offset term defined by:

$$C \equiv 1 + \sum_{i,j} \alpha_i \alpha_j K(x_i, x_j)$$

The Gaussian RBF has one free parameter, called the scale parameter. The scale parameter may affect how tightly the training data is fit and may be a measure of how well the results generalize to unseen data. See also, Banerjee, et al., *A Support Vector Method for Anomaly Detection in Hyperspectral Imagry*, IEEE Trans. Geoscience Remote Sensing, vol. 8(44), pp. 2282-2291 (2006). One possible characterization of the RBF may be done using cross validation or minimax Neyman-Pearson criteria. The SVDD statistics may be compared to a threshold to yield a binary detection image. This may be subject to connected components and morphology (erosion and dilation).

To reiterate, several different algorithms may be utilized for detecting abnormalities in the retinal data. The algorithms may include, for example, a machine learning single class classifier or an anomaly detector algorithm. As shown above, detection algorithms may be based on a support vector data description (SVDD). Additional algorithms may include a support vector machine (SVM), a relevance vector machine (RVM), a neural network, neural analysis, a large margin classifier, a kernel based classifier, a classifier based on a probability density function (PDF) estimator, a classifier based on a Parzen PDF estimator, a Bayesian classifier, a Constant False Alarm Rate (CFAR) detector, a fuzzy logic based classifier, and/or similar detection algorithms.

Intensity Equalization

In one embodiment, an intensity based equalization algorithm may be applied to the image. See Hoover, et al., *Locating the Optic Nerve in a Retinal Image Using the Fuzzy Convergence of the Blood Vessels*, IEEE Transactions on Medical Imaging 22, pp. 951-958 (2003). In one embodiment, the value of each nonzero pixel I(r,c) in the green band of the original image ay be assigned a new value, $I_{eq}(r,c)$, given by:

$$I_{eq}(r,c) = I(r,c) + m - A(r,c)$$

where m is the desired average intensity and A(r,c) is the local average intensity of the pixel. The local average intensity of each pixel may be computed as the average intensity within an N×N neighborhood of each pixel.

Blood Vessel Removal

There are a number of methods for detecting blood vessels in fundus images such as described in Salem, et al., *Segmentation of retinal blood vessels using scale-space features and K-nearest neighbor classifier*, in Proc. 31st International Conference on Acoustics, Speech, and Signal Processing—ICASSP '06, May 14-19, 2006, Toulouse, France; and Chanwimaluang, et al., *An efficient blood vessel detection algorithm for retinal images using local entropy thresholding*, in Circuits and Systems, ISCAS '03, Vol. 5, p. V-21-V-24. 25-28 May 2003. Blood Vessel Removal may be used in one embodiment of this invention, it may be performed as a preprocess or post-process of anomaly detection. Blood vessels may be removed using any existing methods. For example, selecting the green channel and thresholding the image or Canny edge detection followed by morphological processing (erosion and dilation) may be used.

Experiments

Figure 4A:
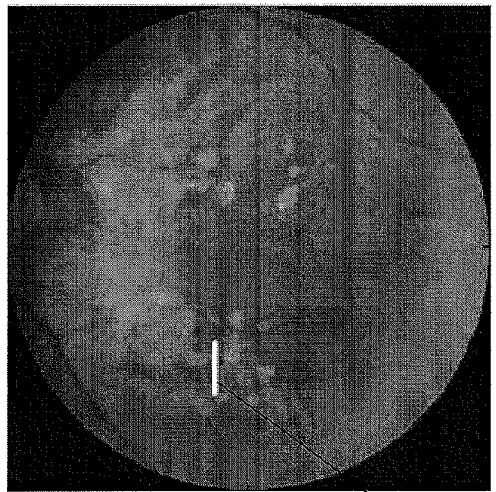
FIGS. 4A, 4B, 4C, and 4D show sample images of (4A & 4C) an original fundus image showing a sample training region and (4B & 4C) corresponding fundus images with anomalous subregions detected according to an embodiment of the current invention.
Figure 4B:
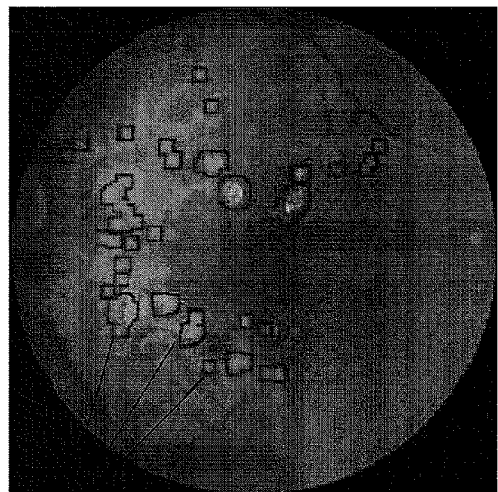
Figure 4C:
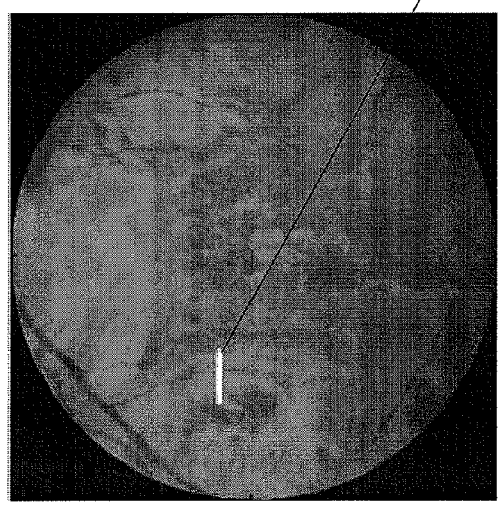

In one illustrative embodiment, for each fundus image the system may train the SVDD on an automatically selected small sliver (an example is shown in FIGS. 4A and 4B, 410) taken from the peripheral area of the retina 210, which may be automatically selected at the same location in each image. It is appropriate to train for background in this area since it is less likely to include drusen 310. The resulting support vectors may then be used to detect possible anomalies in the rest of the image (the training and testing datasets may be kept separate).

Alternately, another method (due to the wide variations in aspect and pigmentations of normal tissue in fundus imagery across individuals) may be to select a subset of images corresponding to healthy individuals for training. Alternatively, another method may be to select training vectors randomly from the periphery of the retina.

Figure 4D:
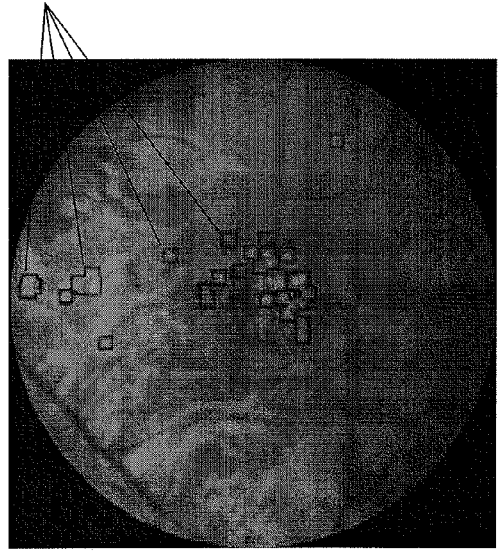

Drusen 310 may also be found in the peripheral area, but the soft-margin SVDD approach may allow the inclusion of outliers in the training set. The test statistic may be thresholded to produce a binary image with normal and anomalous pixels. FIGS. 4B and 4D show an example image with the anomalous subregions delineated 420. In one embodiment, the process of eliminating the blood vessels may be used to suppress some false alarms. In one experiment, the SVDD method has successfully detected drusen 310 for all the AMD fundus images. Table 1 summarizes the experimental results.

TABLE 1

Summary of SVDD training and testing

| Image | Retina | Training vectors | Support vectors | Anomalies found |
|---|---|---|---|---|
| 1 | No-AMD | 600 | 17 | none |
| 2 | AMD | 600 | 10 | yes |
| 3 | AMD | 600 | 16 | yes |
| 4 | AMD | 600 | 30 | yes |
| 5 | AMD | 600 | 20 | yes |
| 6 | AMD | 600 | 2 | yes |
| 7 | Abnormal Pigmentation | 600 | 25 | yes |

Color Based Detection of Drusen

Color may be used as an important visual cue in finding retinal anomalies and characterizing drusen 310. The use of a locally adaptive anomaly detector—instead of a global detector which tested and applied a single decision rule over the entire image—may be used to help abate false positives in images with large illumination gradients or bright flashes. Additionally, the removal of imaging artifacts and specific anatomical features such as vessels or the optic nerve may be used prior to the system being trained to detect abnormalities and may help improve sensitivity and specificity. One embodiment of the present invention may use an algorithm incorporating these capabilities and exploiting color information.

(1) Algorithmic Pipeline

In an illustrative algorithm, the region near the optic nerve may be detected and excluded which may reduce false positives in that area. The image may then be split into gray level and color parts. The grey level image may be used to find training and testing regions of interest (ROIs), while the color image may be converted to Hue Saturation and Value (HSV) space, and the HSV vectors may be used for anomaly detection testing and training. The image may be first processed to put it in a radiometric and geometric canonical form. The grey-level image may be input in a multi-resolution process that looks for ROIs where to apply subsequent testing and training.

ROIs may be found by looking for regions of high gradient magnitude indicative of high-frequency components such as edges. Gradient magnitude may be calculated at different scales of a smooth pyramid decomposition of the fundus image, to address the presence of vessels and features at varying resolutions. Binary ROIs may then obtained by thresholding, and the union of these ROIs may be accumulated at each level of the image pyramid and may yield a ROI termed the master ROI. The master ROI may include drusen 310, and could also include vessels and imaging artifacts as well as some retinal background which may be later dissociated by a parametric and/or non-parametric approach such as a Constant False Alarm Rate (CFAR) anomaly detection scheme. The master ROI binary image may be morphologically closed to create a testing ROI to fill-in hollow drusen 310 and vessel areas. A training ROI may be created by dilating the master ROI and taking its logical complement. This testing ROI should then contain only 'clean' retinal tissue areas which may be generally free of other artifacts.

The testing and training ROIs may then be logically "ANDed" with the original color image converted to HSV space. It may be split into local subimages (e.g., for example, but not limited to, 100×100 windows) where testing and training may occur. Specifically: the H and S channels may be used for training a non-parametric CFAR detector to discriminate based on, for example, color while the value V may be used for training a traditional single-sided CFAR detector, to discriminate based on, for example, intensity. The CFAR detector may be trained on the background V value and would then split regions into low V (generally low intensity corresponding to, e.g., for example, but not limited to, vessels or hyper-pigmentations) and high V values (corresponding to, for example, but not limited to, drusen 310). Pixels found to be anomalous under both CFAR detectors may then be combined and the image may be reconstructed from its subwindows.

(2) Probabilistic Characterization

Using support vector algorithms for pattern recognition can be seen in Schölkopf, et al., *Estimating the Support of a High-Dimensional Distribution*, Neural Computation 13 (2001), pp. 1443-1471, which is hereby incorporated by reference. The probabilistic characterization and anomaly detection analysis, used in one embodiment of this invention, may be performed using a single class SVM approach as follows.: An illustrative training vector may consist of set T of L vectors $x_i$ drawn from an underlying probability distribution P of normal background retinal tissue pixels:

$$T = \{x_i \in R^N, i=1, 2, \ldots L\}$$

In this example, N may equal 2 if $x_i$ consists of the Hue (H) and Saturation (S) values. The support region in feature space of the probability distribution P may be found by using a constrained optimization approach. This approach could construct a support region R in such a way that the probability that a point x drawn from P would have a specified and bounded probability (a False Alarm rate) to lie outside of R (equal to a parameter υ to be described later).

This approach could use a Gaussian Radial Basis Function (RBF) expressed as:

$$K(x,y) = \exp(-\|x-y\|^2/\sigma^2) = \langle \Phi(x), \Phi(y) \rangle$$

in place of the traditional linear dot product $\langle x,y \rangle$. This would thereby map the exemplars inside T from input space onto a infinite-dimensional hypersphere of unit-radius in feature space (since $K(x,y)=1$). In feature space, a hyperplane could be defined as:

$$\langle w, \Phi(x) \rangle = \rho$$

One may seek an hyperplane that would maximally separate the origin from the training exemplars in T, thereby maximizing the distance $\rho/\|w\|$ from the origin to the separating hyperplane. Based on this, the decision region for testing would be $$R = \{x : \mathrm{sgn}(\langle w, \Phi(x) \rangle - \rho) \geq 0\}$$

where sgn(.) denotes the sign function. To complete the specification of R, a certain fraction $\upsilon \in [0,1]$ of the vectors in T may be allowed to violate the original constraint that they must lie within the half space R, i.e., they may satisfy instead that:

$\langle w, \Phi(x_i) \rangle \geq \rho - \xi_i$, for some positive distance $\xi_i \geq 0$ These specifications may be summarized in a constrained minimization of the following quadratic objective function:

$$\min_{w \in F, \xi \in {}^lL, \rho \in \prime} \frac{1}{2}\|w\|^2 + \frac{1}{\upsilon L}\sum_i \xi_i - \rho$$

subject to constraints:

$$\langle w, \Phi(x_i) \rangle \geq \rho - \xi_i, \xi_i \geq 0.$$

Note that when $\upsilon$ is small, the penalty imposed on the points violating the separating plane may increase. To solve this constrained problem a Lagrangian is defined as:

$$L(w, \xi, \rho, \alpha, \beta) = \frac{1}{2}\|w\|^2 + \frac{1}{\upsilon L}\sum_i \xi_i - \rho + A(w, \xi, \rho, \alpha, \beta, x)$$

$$A(w, \xi, \rho, \alpha, \beta, x) = -\sum_i \alpha_i(\langle w, \Phi(x) \rangle - \rho + \xi_i) - \sum_i \xi_i \beta_i$$

Which may invoke the Kuhn-Tucker conditions, because of the complementary slackness constraint, a certain number of the Lagrange multipliers $\alpha_i$ may be non-zero, these correspond to exemplars that may lie on the hyperplane boundary of R, and may be called support vectors. For example, taking the first order optimality condition and setting the partial derivative of the Lagrangian to w.r.t. $(w, \xi, \rho, \alpha, \beta)$ to zero, the following properties may follow:

$$w = \sum_i \alpha_i \Phi(x_i), \sum_i \alpha_i = 1$$

Therefore, the optimal vector w may be the weighted average (center of mass) of the support vectors. Finally, plugging back the last equation, in the definition of R:

$$R = \left\{ x : \sum_i \alpha_i K(x_i, x) \geq \rho \right\}$$

The decision region R may have a probabilistic interpretation by reading the term $$\sum_i \alpha_i K(x_i, x)$$

as being a mixture of Gaussians and therefore R as region resulting from a CFAR detection rule.

R as defined directly above (e.g., for example, but not limited to, based on color) may include feature vectors of drusen 310 pixels as well as pixels corresponding to vessels, imaging artifacts, other pigmentations or other pathologies. Deciding between these various cases may be accomplished by adopting an additional CFAR test on the intensity. The intensity (value in HSV) may be assumed Gaussian, therefore the mean and variance may be computed and a one-sided detection region $R_F$ catching drusen 310 which may be of higher intensity when compared to these other classes, and defined as $$R_F = \{V : |v - \bar{v}| \geq T\sigma_v\}$$

An illustrative final detection region may then be taken as $R \cap R_F$ and the decision to classify the patient as normal or pathological is based on the number of pixels found to be drusen 310 pixels by this rule.

Additional Embodiments

Multi-Resolution Local/Global Detection

Figure 7A:
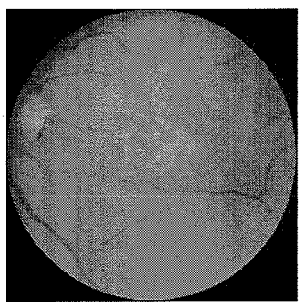
FIGS. 7A, 7B, 7C, 7G, 7H, and 7I illustrate six different fundus images.
Figure 7B:
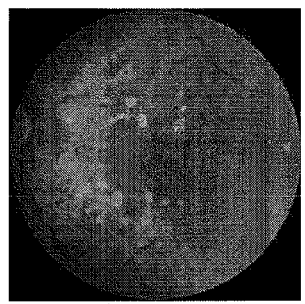
Figure 7C:
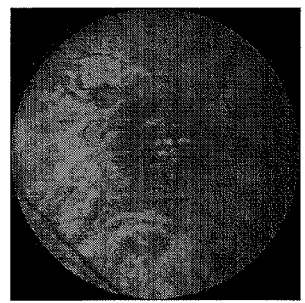
Figure 7D:
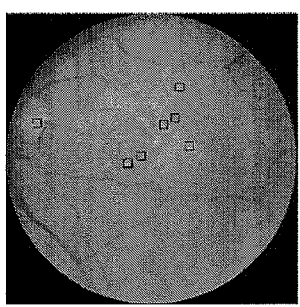
FIGS. 7D, 7E, 7F, 7J, 7K, and 7L illustrate corresponding fundus images with anomalous subregions detected according to an embodiment of the current invention.
Figure 7E:
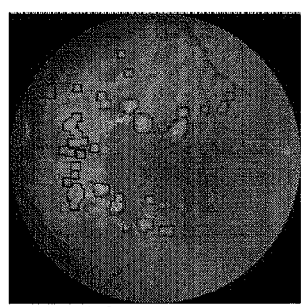
Figure 7F:
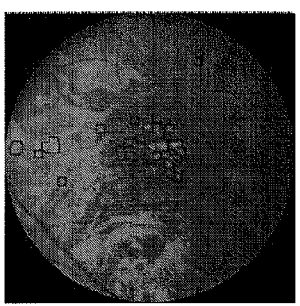
Figure 7G:
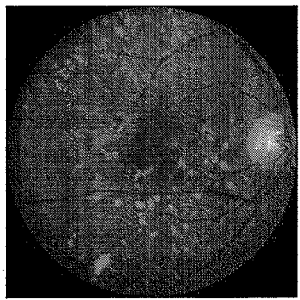
Figure 7H:
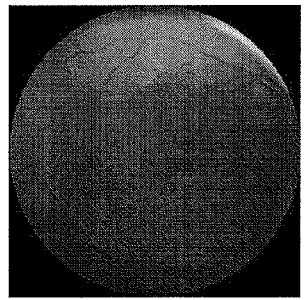
Figure 7I:
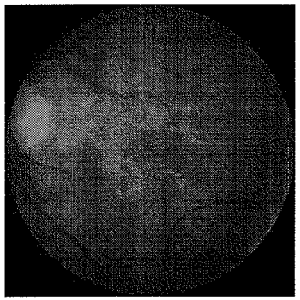
Figure 7J:
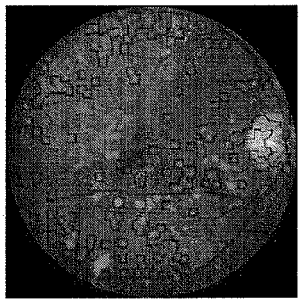
Figure 7K:
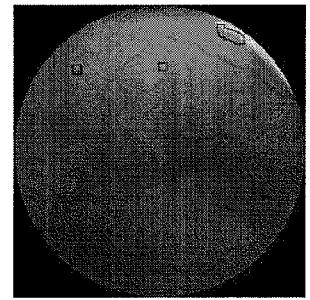
Figure 7L:
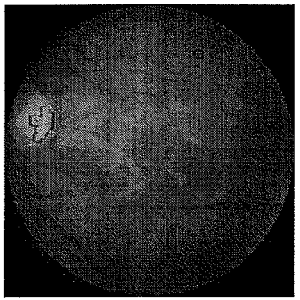

When performing global anomaly detection, SVDD may be used to create a global statistical model (i.e., for example, generated over the entire image) to describe normalcy. Global detection may have advantages, for example, but not limited to, simplicity, speed, efficiency, and lower false positive rates in some situations. It may also have drawbacks. For instance, bright regions such as the example appearing at 2 o'clock in the fundus image shown in FIG. 7H could sometimes be detected as globally anomalous when training occurs in a normal area of the retina that does not include these artifacts. One way to partially deal with these issues may be to perform random sampling.

Another possible embodiment may include exploiting a locally adaptive anomaly detection scheme. For example, a pixel may be tested against a model derived from a hollow local neighborhood sampling window. Locally bright backgrounds or local bright flashes may appear as locally normal to local anomaly detectors, and may be less likely to generate false positives. Similarly, for local anomaly detectors, the detection of drusen 310 may adapt to the local background intensity, allowing for improved detection in images with smooth background intensity gradient. However, local anomaly detection may have the drawback that confluent large drusen may appear normal to a local detector using a window size smaller than the druse. In one embodiment, the issue with large drusen may be overcome by applying a hybrid detector which may operate mid-way between a local and global and also using a multi-resolution scheme whereby different resolution sampling windows and detectors may be used, and the detection results obtained at each scale may then be fused together.

Kernel Scale Selection

In one embodiment of the present invention, any outstanding tuning parameter may be automatically selected. One parameter that may be adjusted is the SVDD kernel scale. The selection of the scale for RBF kernels may be important in SVM or SVDD methods because it may affect the number of support vectors selected and the generalization and overfitting properties of the method. Developed methods such as, for example, those based on cross-validation or leave-one-out approaches may be used, as well a procedure relying on artificial insertion of statistical outliers, to find the best tuning for the kernel scale parameters.

Best Feature Selection

Another embodiment of the invention may use various features, such as color, texture, gradient, and may rank them in importance depending on the patient specifics, such as, but not limited to, ethnic background, presence of other pathologies, illumination conditions, etc. Illumination conditions may include, but are not limited to, focus, sharpness, contrast, presence of extraneous artifacts, etc. The robustness of the features may be altered depending on context, to allow their optimal combination.

Image Analysis Architecture

In another embodiment, both the components from our global algorithm which performs intensity and texture discrimination through wavelets and our local algorithm which may be primarily concerned with color and intensity, may be combined into a single algorithm working at different local/global multi-resolution levels.

Stereo Images

Other embodiments may include stereo image pairs. Imaging quality for the right and left images are often dissimilar. Their combination could therefore provide benefits by exploiting diversity and increasing SNR. Another embodiment may include depth reconstruction for detection of drusen and other retinal abnormalities.

Image Pairs

Often, the presence of drusen in one eye correlates with drusen presence in the other eye (since about half of the subjects with advanced stage in one eye will develop within 5 years the advanced stage in the second eye). One embodiment of our invention may exploit this fact in a probabilistic Bayesian framework with the presence of drusen in one eye providing a prior probability for detecting it in the other.

Image Quality Pre-Screening

Another embodiment may have a module to pre-screen the fundus image to rate its quality (e.g., but not limited to, sharpness, focus, contrast, presence of artifacts due to illumination such as bright flashes). For example, if the image quality is deemed too poor, it may automatically trigger a reacquisition of the fundus image by the system, ensuring a consistent performance results.

Eye Feature Detection and Removal

It may be important to dissociate typical features such as optical nerve, spurious but non-pathological pigmentations, blood vessels, or other lesions associated to other pathologies such as diabetic retinopathy, from drusen 310. This may be done as by, for example, the CFAR. Additional steps may be incorporated based on existing techniques that have been designed explicitly for finding anatomical features of the wet form or abnormal blood vessels, such as subretinal or intraretinal fluid or blood or scar tissue such as those proposed in Age-Related Eye Disease Study Research Group.

Registration

In one embodiment of the present invention, geometric registration, also termed alignment, of fundus images of the same eye may be used. Stereo pairs, if used jointly, may have established geometric alignment parameters between a right and left image. Also, a longitudinal study of the same patient may be used and the successive tempora images may be registered to detect changes (change detection). Extraneous changes in imaging conditions and progression of the disease may be two factors that may impair the alignment process. These problems may be fixed through, for example, image registration. For fundus image registration, two geometric projections may be considered; the system may, for example, align the two images in the 2D image domain (direct image registration). Since these are images of the retina, another refinement may be used which consists of back projecting the images into a half sphere to perform the registration in that manifold (a spherical image registration). When doing registration, one consideration may be the type of transformation used for bringing the two images in alignment. For direct image registration, a similarity transformation (consisting of rotation, translation and scaling) may be used, and for spherical image registration, scaling and rotation may be used. Another consideration may be the choice of distance measure used to assess the quality of the alignment. For this mutual information may be used. Mutual information is defined as $\mu_{I,I'} = E_I + E_{I'} - E_{I,I'}$ where E denotes the marginal and joint entropies.

Increasing image similarities under a transformation able to correctly align images would yield smaller joint entropy, which in turn would yield larger mutual information. Statistical distributions may be computed empirically by using the joint and marginal histograms. The entropies may then be obtained as $$E_I = \sum_k h_I(k) \log h_I(k),$$

$$E_{I'} = \sum_k h_{I'}(k) \log h_{I'}(k),$$

$$E_{I,I'} = \sum_{k,l} h_{I,I'}(k) \log h_{I,I'}(k)$$

Since mutual information is a global measure, it may be robust to changes due to the disease progression (aggravation or improvement) or the presence of imaging artifacts. Since it may measure the statistical co-occurrence of radiance values in both images using entropy, mutual information may be robust to changes in imaging (illumination, contrast, sharpness) conditions.

Additional Detection

According to another embodiment, detection of abnormalities may not be limited to detection of drusen and AMD. Other abnormalities that may be detected may include diabetic retinopathy, retinal vein occlusions, a vitreomacular interface abnormality, a macular hole, an epiretinal membrane, optic nerve pathologies, glaucomatous optic nerve damage, and/or other pathologies.

Additional Analysis

In another embodiment, the patient's eye, retina, and/or fundus may be subject to optical coherent tomography, a fundus imager, a non-mydriatic fundus imager, a mydriatic fundus imager, a monochromatic imager, a portable optical coherence tomography machine, a multispectral camera, a hyperspectral sensor, a scanning laser ophthalmoscopy system, an eye fundus angiography system, a stereoscopic imaging system, or a multi-modality system (e.g., a system that combines multiple types of scanning and imaging). These devices may produce one or more images (e.g., such as a standard fundus image, a non-mydriatic fundus image, a mydriatic fundus image) of the eye, retina, and/or fundus. Alternatively, these devices may create enhanced retinal data that represents information about the eye, retina, and/or fundus.

In another embodiment, the retinal data may be analyzed by detecting and excluding a non-pathological anatomical feature. Data analysis may also include detecting and excluding from the retinal data an optic disk region near an optic nerve, a non-pathological pigmentation, a lesion, or a blood vessel. Data analysis may include selecting from a local region that was parsed in order to identify and/or exclude all anomalies.

Data analysis may include using and selecting a subset of normal pixels for training from a prescribed region of the retinal image, a random selection of pixels from the retinal image, or a set of preexisting normal training images.

Analyzing of the retinal data and/or a retinal image may also include using the full RGB data or extracting the green, red and/or blue channels, linear filtering, spectral filtering, nonlinear filtering, low pass filtering, median filtering, performing intensity remapping, performing histogram equalization, performing contrast stretching, performing adaptive histogram equalization, normalizing the data, whitening the data, performing image enhancement, performing thresholding, performing image registration and matching, performing remapping of the original red, green, and blue (RGB) color space into another color space (such as, but not limited to, Hue/Saturation/Value or CYMK), performing stochastic classification of the pixels into different classes (classes may include vessels, background, drusen, etc.), performing band selection on the retinal data, performing dimensionality reduction on the retinal data, performing best feature selection using principal component analysis (PCA), performing best feature and classifier selection using Boosting, performing edge detection, computing the gradient, computing the Hessian, performing global static window analysis, performing local static window analysis, performing local sliding window analysis, comparing the features' PDFs using histograms, comparing the features' PDFs using mutual information, comparing the features' PDFs using correlation, comparing the features' PDFs using Kullback-Leiber (KL) distance, using segmentation of the retinal data, segmenting retinal anatomical features, segmenting the retinal vasculature, segmenting the fovea, creating a feature vector, performing connected components on the anomalous pixels to obtain anomalous blobs, creating a feature vector composed of the original single band data, creating a feature vector composed of the original multi band data, creating a feature vector composed by downselecting the original multi band data, creating a feature vector composed of the output of filtering the original data, creating a feature vector composed of a wavelet analysis of the original data, creating a feature vector composed of a statistical measure derived from a single or multiple bands of the data, creating a feature vector composed of morphological features of the data, creating a feature vector composed of a shape features of the anomalous blobs, creating a feature vector composed of an area of detected objects, using binary level mathematical morphological operations, using grey level mathematical morphological operations, using binary level mathematical morphological filters, using grey level mathematical morphological filters, performing intensity equalization, performing texture analysis, obtaining a wavelet signature of pixels, performing multi-resolution processing, or creating a feature vector. Additionally, performing global or local static or sliding window analysis for any of these previously mentioned processes may also be a possibility. Further operations may include using binary or grey level mathematical morphological operations or morphological filters including but not limited to dilation, erosion, opening, closing, top-hat, bottom hat, gradient, watershed, flood fill, distance transforms and ultimate erosions. Additional operations may include creating a feature vector which may be composed of the original bands, the down selected bands, the filtered bands (e.g. wavelets) and/or statistical measures (mean, variance, and any higher order moment, mode, median value) derived from these image bands, and/or morphological and shape features such as length, area of detected objects.

In another embodiment, the image could be further analyzed using additional semi-automated, user in the loop manual steps in addition to the automated steps previously mentioned.

In yet another embodiment, detecting an abnormality may include global anomaly detection analysis, or local anomaly detection analysis. The detecting may also include detection based on color, texture, intensity, depth, or gradient. Detecting may also be based on a longitudinal study which may include comparing the retinal data with other retinal data (possibly previously acquired) and detecting an abnormality in the retinal data based on counting pixels or change detection.

In another embodiment, detecting abnormalities may be assisted, or algorithms may be tuned, by the inclusion of information such as demographic information, age data, race data, ocular information, ph level, ocular pressure, arterovenous ratio, systemic factors, body mass index data, blood pressure data, genetic information, family history data, or a patient severity scale, for example.

Yet another embodiment of the current invention may include a stand alone software system able to detect AMD and taking as input electronic fundus images acquired at a remote site (as opposed to a system coupled to a fundus imager).

Yet another embodiment of the current invention may include a stand alone software system designed specifically to perform longitudinal studies of AMD and other retinal pathologies. This system will assist a clinician by quantifying the progression of the disease and may be used for clinical purposes, research purposes or for evaluating different treatment options.

Yet another embodiment of the current invention may include a stand alone system delivered as a kiosk that may be placed in public areas (for example malls, walk in clinics) that performs detection of AMD and other retinal abnormalities.

Example Procedure for Automated Detection of Drusen in Fundus Images

Figure 5A:
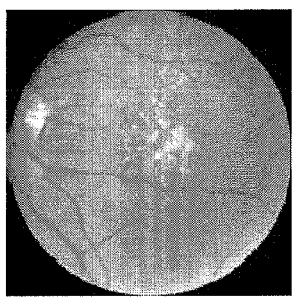
FIGS. 5A, 5B, 5C, 5D, 5E, and 5F illustrate sample preprocessing performed according to an embodiment of the current invention on a fundus image of (5A) a raw fundus image with an illustrative Green band selected, (5B) an intensity equalized fundus image, (5C) a fundus image with a wavelet signature for 10 pixel dilation applied, (5D) a fundus image with a wavelet signature for 40 pixel dilation applied, (5E) a fundus image with a wavelet signature for 70 pixel dilation applied, and (5F) a fundus image with a wavelet signature for 100 pixel dilation applied.
Figure 5B:
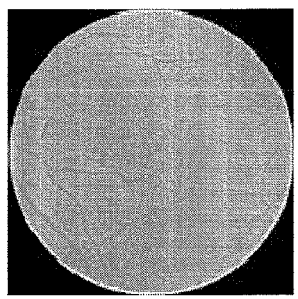
Figure 5C:
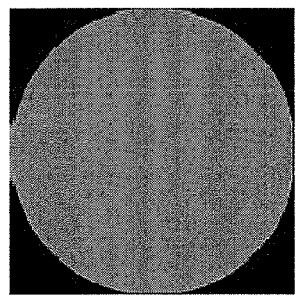
Figure 5D:
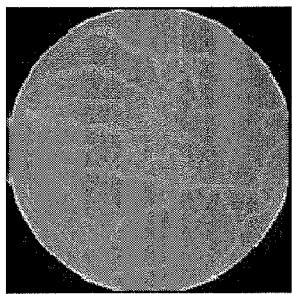
Figure 5E:
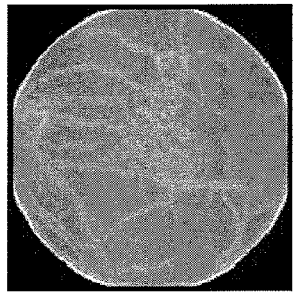
Figure 5F:
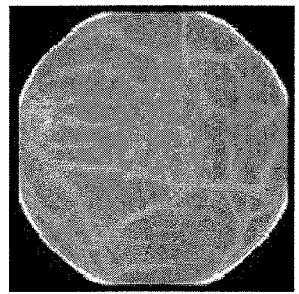
Figure 6A:
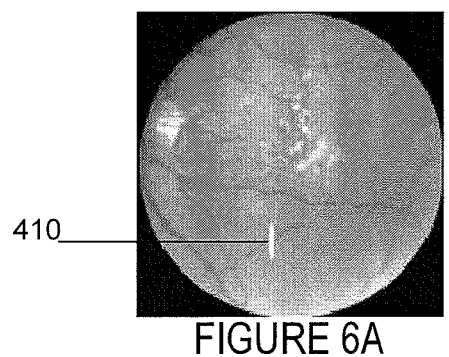
FIGS. 6A and 6B show the first and last steps in Support Vector Data Description (SVDD) training and testing according to an embodiment of the current invention, (6A) shows an illustrative white vertical line depicting the region where training samples may be collected and (6B) depicts an example of the results after testing has been performed.
Figure 6B:
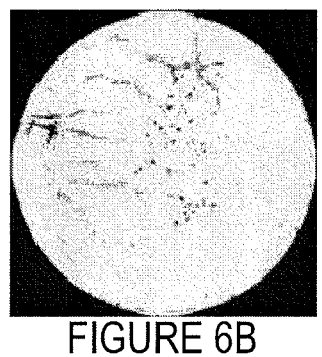
Figure 8:
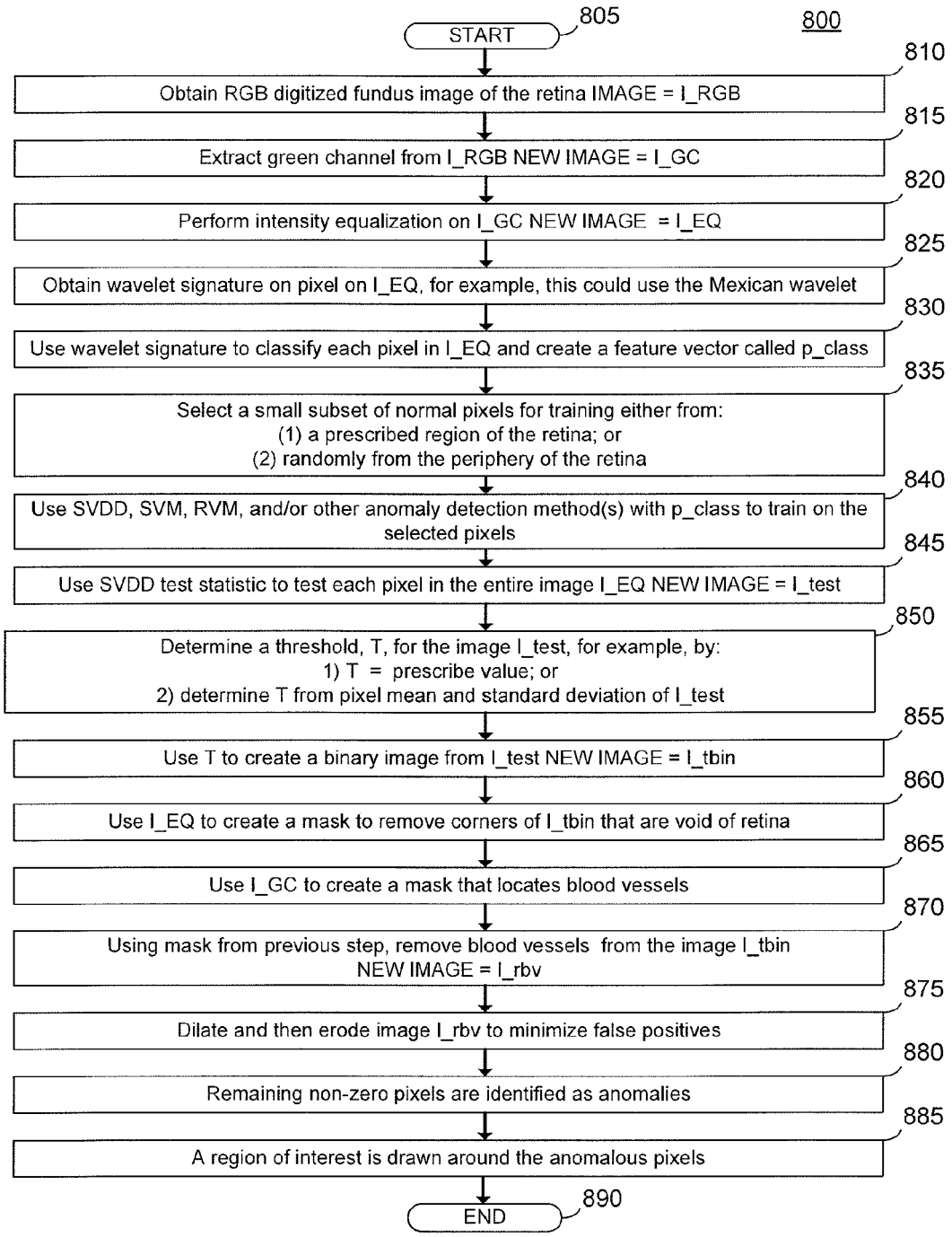
FIG. 8 depicts an illustrative flowchart according to an embodiment of the current invention.

FIG. 8 depicts an illustrative flowchart 800 for one embodiment of our automated detection of drusen in fundus images and starts at 805. From 805 flow may move to 810 where a digitized fundus image of a retina may be obtained 300. From 810 flow may move to 815 where the green channel may be extracted from the original fundus image of a retina and a new image may be created FIG. 5A. From 815 flow may move to 820 where intensity equalization may be performed on the green channel image and a new image may be created (FIG. 5C). From 820 flow may move to 825 where wavelet filtering may be performed to obtain wavelet signature of pixels. Such wavelets may include the Mexican hat wavelet as depicted in FIG. 13. From 825 flow may move to 830 where the wavelet signature may be used to classify each pixel from the intensity equalization image and a feature vector called p_class may be created. From 830 flow may move to 835 where a small subset of normal pixels for training may be selected from either a prescribed region of the retina or from a random selection of the periphery of the retina. From 835 flow may move to 840 where the SVDD method with the p_class may be used to train on the selected pixels. From 840 flow may move to 845 where the SVDD test statistic may be used to test each pixel in the entire intensity equalization image and a new image may be created. From 845 flow may move to 850 where a threshold, T, may be determined by some method (for example, this could be a prescribed value or may be determined from pixel mean and standard deviation of the SVDD test statistic image created in step 845.) From 850 flow may move to 855 where T may be used to create a binary image from the SVDD test statistic image created in step 845 and a new image may be created. From 855 flow may move to 860 where the intensity equalization image may be used to create a mask to remove corners of the binary image from 855 that are void of retina. From 860 flow may move to 865 where the green channel image may be used to create a mask that locates blood vessels. From 865 flow may move to 870 where the blood vessel mask may be used to remove blood vessels from the binary image from 855 and may create a new image. From 870 flow may move to 875 where the blood vessel removed image from 870 may be dilated and its image eroded to minimize false positives. From 875 flow may move to 880 where the remaining non-zero pixels may be identified as anomalies. From 880 flow may move to 885 where a region of interest may be drawn around the anomalous pixels, as shown in 420 (FIGS. 4B and 4D). From 885 the flow ends at 890.

Figure 9:
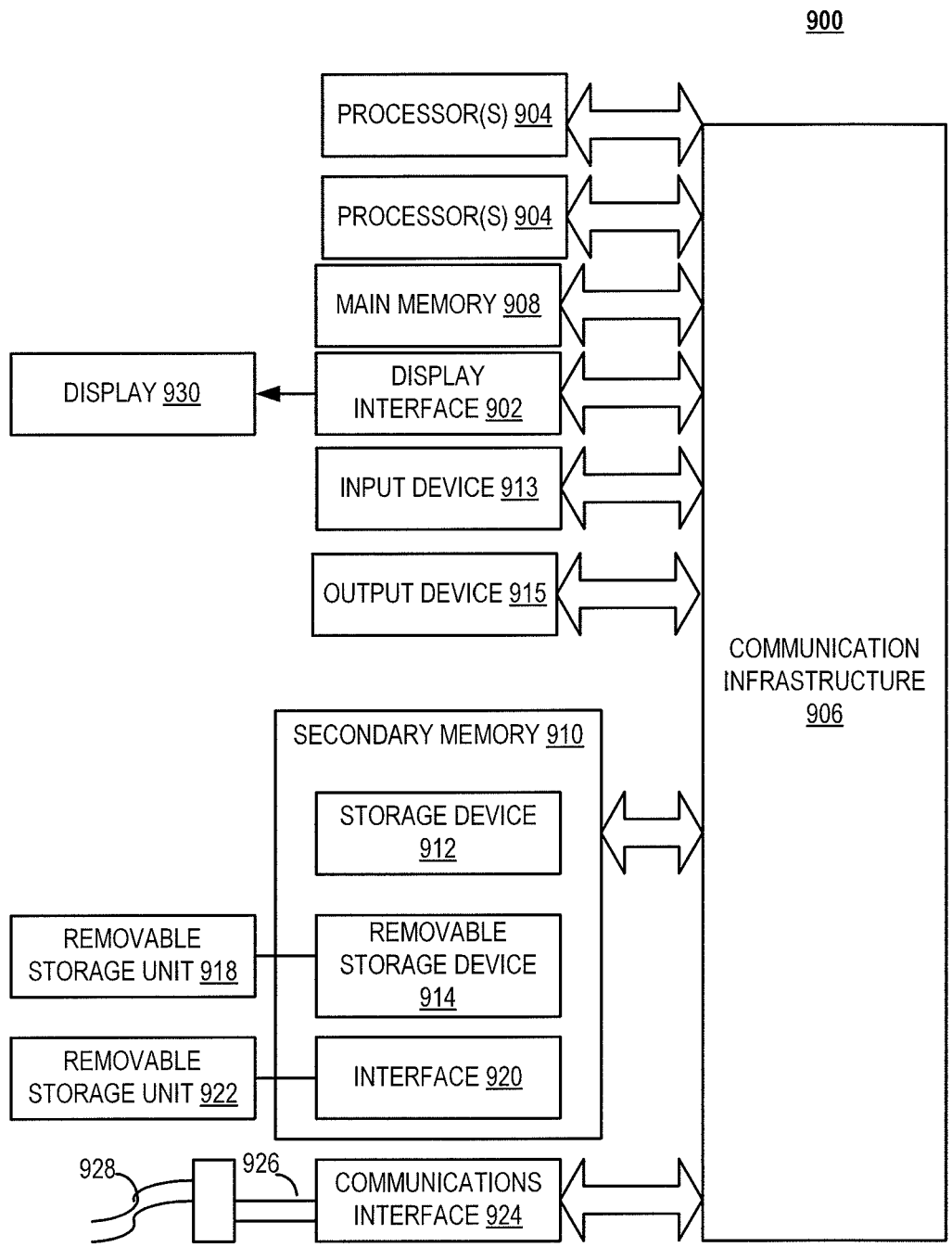
FIG. 9 depicts an example computer system that may be used in implementing an illustrative embodiment of the present invention.

FIG. 9 depicts an illustrative computer system that may be used in implementing an illustrative embodiment of the present invention. Specifically, FIG. 9 depicts an illustrative embodiment of a computer system 900 that may be used in computing devices such as, e.g., but not limited to, standalone or client or server devices. FIG. 9 depicts an illustrative embodiment of a computer system that may be used as client device, or a server device, etc. The present invention (or any part(s) or function(s) thereof) may be implemented using hardware, software, firmware, or a combination thereof and may be implemented in one or more computer systems or other processing systems. In fact, in one illustrative embodiment, the invention may be directed toward one or more computer systems capable of carrying out the functionality described herein. An example of a computer system 900 is shown in FIG. 9, depicting an illustrative embodiment of a block diagram of an illustrative computer system useful for implementing the present invention. Specifically, FIG. 9 illustrates an example computer 900, which in an illustrative embodiment may be, e.g., (but not limited to) a personal computer (PC) system running an operating system such as, e.g., (but not limited to) MICROSOFT® WINDOWS® NT/98/2000/XP/Vista/Windows 7/etc. available from MICROSOFT® Corporation of Redmond, Wash., U.S.A. However, the invention is not limited to these platforms. Instead, the invention may be implemented on any appropriate computer system running any appropriate operating system. In one illustrative embodiment, the present invention may be implemented on a computer system operating as discussed herein. An illustrative computer system, computer 900 is shown in FIG. 9. Other components of the invention, such as, e.g., (but not limited to) a computing device, a communications device, a telephone, a personal digital assistant (PDA), a personal computer (PC), a handheld PC, a laptop computer, a netbook, client workstations, thin clients, thick clients, proxy servers, network communication servers, remote access devices, client computers, server computers, routers, web servers, data, media, audio, video, telephony or streaming technology servers, etc., may also be implemented using a computer such as that shown in FIG. 9.

The computer system 900 may include one or more processors, such as, e.g., but not limited to, processor(s) 904. The processor(s) 904 may be connected to a communication infrastructure 906 (e.g., but not limited to, a communications bus, cross-over bar, or network, etc.). Processors 904 may also include multiple independent cores, such as a dual-core processor or a multi-core processor. Processors 904 may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

Computer system 900 may include a display interface 902 that may forward, e.g., but not limited to, graphics, text, and other data, etc., from the communication infrastructure 906 (or from a frame buffer, etc., not shown) for display on the display unit 930.

The computer system 900 may also include, e.g., but is not limited to, a main memory 908, random access memory (RAM), and a secondary memory 910, etc. The secondary memory 910 may include, for example, (but is not limited to) a hard disk drive 912 and/or a removable storage drive 914, representing a floppy diskette drive, a magnetic tape drive, an optical disk drive, a compact disk drive CD-ROM, etc. The removable storage drive 914 may, e.g., but is not limited to, read from and/or write to a removable storage unit 918 in a well known manner. Removable storage unit 918, also called a program storage device or a computer program product, may represent, e.g., but is not limited to, a floppy disk, magnetic tape, optical disk, compact disk, etc. which may be read from and written to removable storage drive 914. As will be appreciated, the removable storage unit 918 may include a computer usable storage medium having stored therein computer software and/or data.

In alternative illustrative embodiments, secondary memory 910 may include other similar devices for allowing computer programs or other instructions to be loaded into computer system 900. Such devices may include, for example, a removable storage unit 922 and an interface 920. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units 922 and interfaces 920, which may allow software and data to be transferred from the removable storage unit 922 to computer system 900.

Computer 900 may also include an input device such as, e.g., (but not limited to) a mouse or other pointing device such as a digitizer, and a keyboard or other data entry device (none of which are labeled). Other input devices 913 may include a facial scanning device or a video source, such as, e.g., but not limited to, fundus imager, a retinal scanner, a web cam, a video camera, or other camera.

Computer 900 may also include output devices, such as, e.g., (but not limited to) display 930, and display interface 902. Computer 900 may include input/output (I/O) devices such as, e.g., (but not limited to) communications interface 924, cable 928 and communications path 926, etc. These devices may include, e.g., but are not limited to, a network interface card, and modems (neither are labeled). Communications interface 924 may allow software and data to be transferred between computer system 900 and external devices.

In this document, the terms "computer program medium" and "computer readable medium" may be used to generally refer to media such as, e.g., but not limited to removable storage drive 914, and a hard disk installed in hard disk drive 912, etc. These computer program products may provide software to computer system 900. Some embodiments of the invention may be directed to such computer program products. References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an illustrative embodiment," do not necessarily refer to the same embodiment, although they may. In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still co-operate or interact with each other.

An algorithm is here, and generally, considered to be a self-consistent sequence of acts or operations leading to a desired result. These include physical manipulations of physical quantities. Usually, though not necessarily, these quantities take the form of electrical or magnetic data capable of being stored, transferred, combined, compared, and otherwise manipulated. It has proven convenient at times, principally for reasons of common usage, to refer to these data as bits, values, elements, symbols, characters, terms, numbers or the like. It should be understood, however, that all of these and similar terms are to be associated with the appropriate physical quantities and are merely convenient labels applied to these quantities.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments of the present invention may include apparatuses for performing the operations herein. An apparatus may be specially constructed for the desired purposes, or it may comprise a general purpose device selectively activated or reconfigured by a program stored in the device.

In yet another illustrative embodiment, the invention may be implemented using a combination of any of, e.g., but not limited to, hardware, firmware and software, etc.

Figure 10:
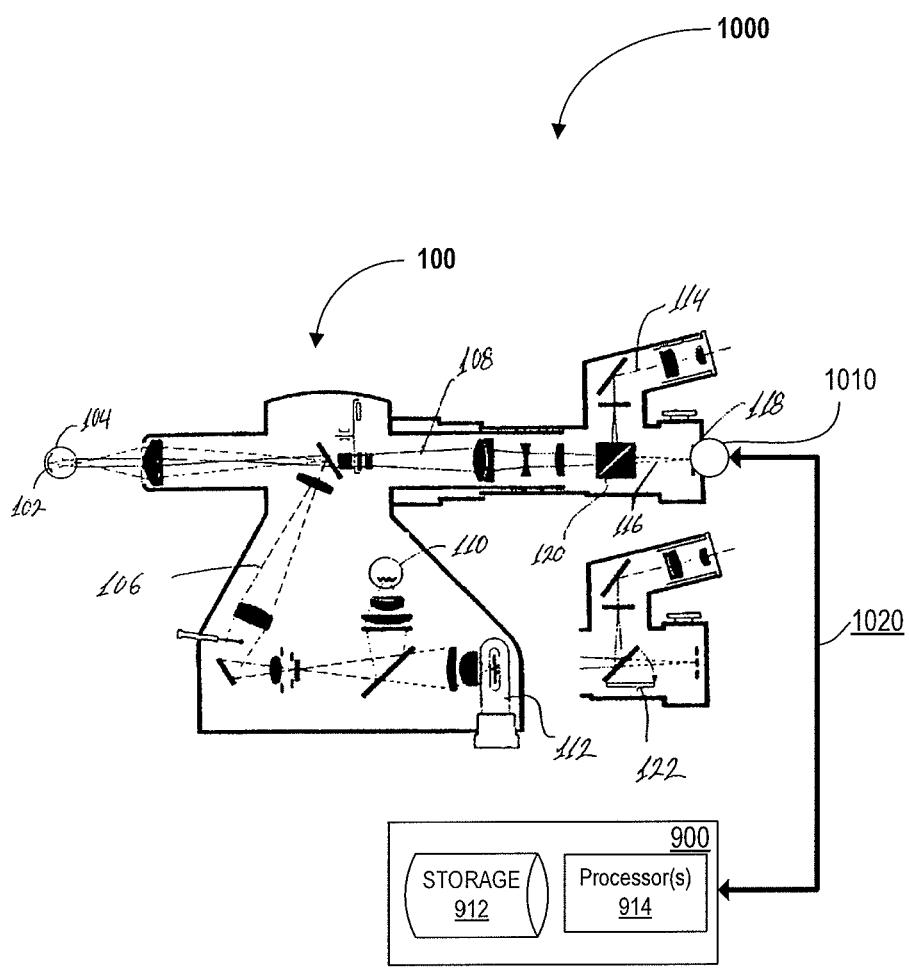
FIG. 10 depicts an example fundus imager coupled to an example computer system according to an illustrative embodiment of the present invention.

FIG. 10 depicts an illustrative computer system 900 coupled to an illustrative fundus imager 100 that may be used in implementing an illustrative embodiment of a retina abnormality detection system 1000 according to an example of an embodiment of the present invention. Illustrative computer system 900 and illustrative fundus imager may be coupled via communications path 1020. Communications path may be, but is not limited to, optical (e.g., fiber optic), electrical (e.g., electrically conductive wire), or electromagnetic (e.g., wireless transmission). The fundus image taken by 100 may be converted into a form recognized by illustrative computer system 900 (e.g., not limited to, binary encoded, Exif, JPEG, TIFF, RAW, PNG, BMP, GIF, SVG). Connector 1010 may be used to send a fundus image in a format recognizable by illustrative computer system 900. Illustrative computer system 900 may receive a fundus image via communications path 1020 and may store image in storage 912.

Figure 11:
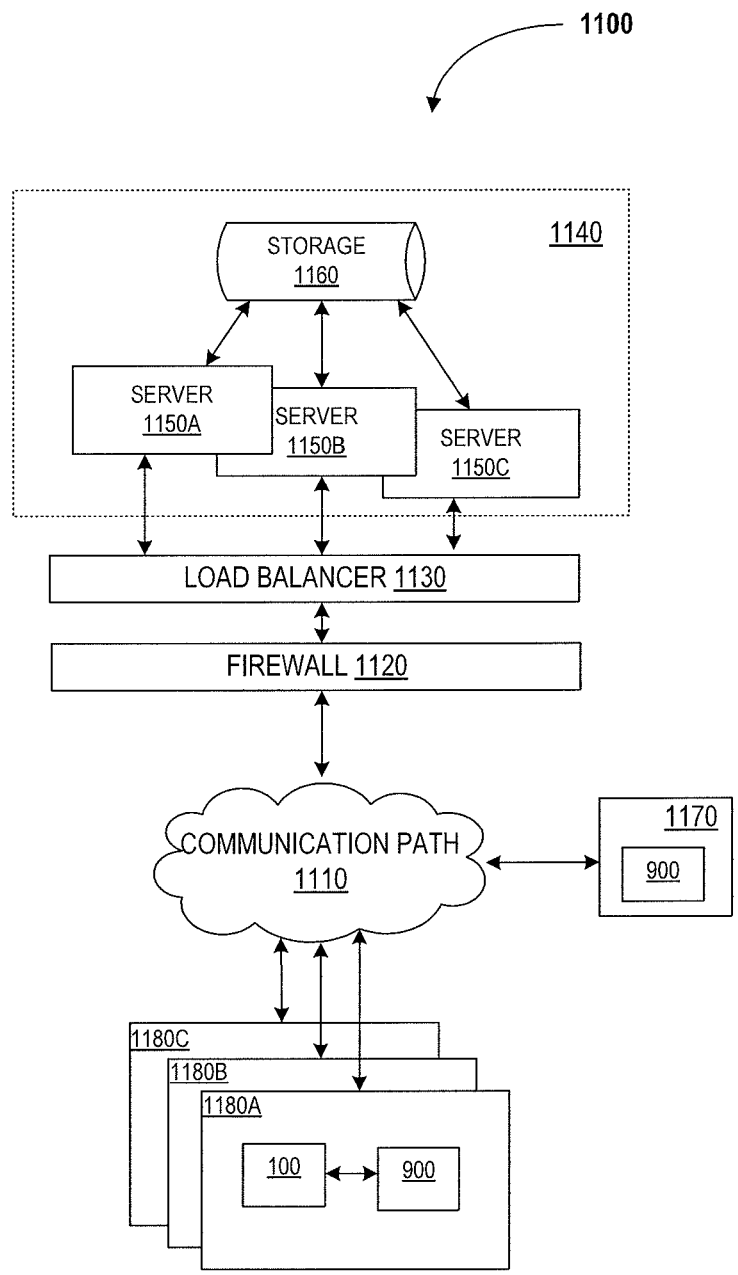
FIG. 11 depicts an example high-level view of an illustrative embodiment of a distribution system according to an illustrative embodiment of the present invention.

FIG. 11 depicts a high-level view of an illustrative embodiment of a possible network distribution system 1100 according to an example of an embodiment of the present invention. An illustrative embodiment provides for a client-server network design with back-end services and processing and may consist of one or more servers 1150A, 1150B, 1150C, etc. (collectively 1150) which may consist of both application and webservers and may have a physical or logical storage unit 1160.

In an illustrative embodiment, a service provider 1140 may create, store, and compress for electronic transmission or distribution fundus image and abnormality information. A service provider 1140 may receive and decompress electronic transmissions from clients, system maintainers, or other interested individuals. The physical or logical storage unit 1160 may, for example, store sample instructional video clips, photographs, fundus images, marketing information, product information, institutional data, physician data, eye care specialist data, client data, etc. The server 1150 may be coupled to client devices 1180A-1180C and 1170 through a communications path 1110 (e.g., but not limited to the internet) via a load balancer 1130 and a firewall 1120. According to another embodiment, the distribution system 1100 could be represented by any of a number of well known network architecture designs including, but not limited to, peer-to-peer, client-server, hybrid-client (e.g., thin-client), or standalone. A standalone system (not shown) may exist where information and updates are distributed via a medium such as, e.g., a computer-readable medium, such as, e.g., but not limited to, a compact disc read only memory (CD-ROM), and/or a digital versatile disk (DVD), etc. Any other hardware architecture such as, e.g., but not limited to, a services oriented architecture (SOA) by one skilled in the art could also be used.

According to one embodiment, a system maintainer device such as depicted as 1170 may provide updated abnormality searching and detection algorithms, instructional information, videos, product information, institutional data, physician data, eye care specialist data, client data, etc. to the system 1100. The maintainer device 1170 may be a computing device 900 or any other device capable of interacting with a network such as the communications path 1110.

The multiple client devices 1180A, 1180B, 1180C, etc., hereinafter collectively referred to as 1180, may exist in system 1100. Client device 1180 may be a computing device 900 combined with fundus imager 100 as illustrated in 1000 (or any other device capable of interacting with a network such as the communications path 1110). Client device 1180 will typically allow an individual to have a fundus image created and analyzed. This image may be stored at a globally accessible location such as in storage 1160. This would allow for transmission of the fundus image to, for example, an eye specialist or physician for additional analysis. Also, storage of fundus image would allow for tracking of changes to the patient's fundus over time.

Client device 1180 may also be capable of receiving information from storage 1160. Such information may include, but is not limited to, software updates (including improvements in detecting abnormalities), marketing material, updated instructional material, etc.

In one illustrative embodiment, storage device 1160 may include a storage cluster, which may include distributed systems technology that may harness the throughput of, e.g., but not limited to, hundreds of CPUs and storage of, e.g., but not limited to, thousands of disk drives. As shown in 1100 content file upload and download operations may be delivered via one or more load balancing devices 1130. In one exemplary embodiment, the load balancer 1130 may include a layer four ("L4") switch. In general, L4 switches are capable of effectively prioritizing TCP and UDP traffic. In addition, L4 switches, which incorporate load balancing capabilities, may distribute requests for HTTP sessions among a number of resources, such as servers 1160. For this embodiment, the load balancer 1130 may distribute upload and download requests to one of a plurality of servers 1150 based on availability. The load balancing capability in an L4 switch is currently commercially available.

In one embodiment, the storage device 1160 may communicate with servers 1150, maintainer devices 1170, and client devices 1180 via the standard Internet hypertext transfer protocol ("HTTP") and universal resource locators ("URLs"). Although the use of HTTP is described herein, any well known transport protocol (e.g., but not limited to, FTP, UDP, SSH, SIP, SOAP, IRC, SMTP, GTP, etc) may be used without deviating from the spirit or scope of the invention. The client devices 1180 and maintainer device 1170 (i.e., the end-user) may generate hyper text transfer protocol ("HTTP") and/or a proprietary protocol requests to the servers 1150 to obtain hyper text mark-up language ("HTML") files and/or proprietary data files.

Yet another embodiment of the current invention may include a hardware and/or software system able to detect AMD and taking as input electronic fundus images acquired at a remote site. The remote site housing the fundus imager may, for example, be located at an office of a doctor, clinician, health care professional, or eye care specialist, or located at a shopping mall, a department of motor vehicles, grocery store, drug store, etc. The hardware and/or software system able to detect AMD system may be co-located with the fundus imager or may be housed in another facility remotely located from the fundus imager. Images may be transmitted from the fundus imager to the hardware and/or software system able to detect AMD through the Internet, a proprietary network, a dedicated network, or through the use of storage media such as, but not limited to, magnetic media, CD-ROM, DVD, Blue-ray, or flash memory.

Figure 12:
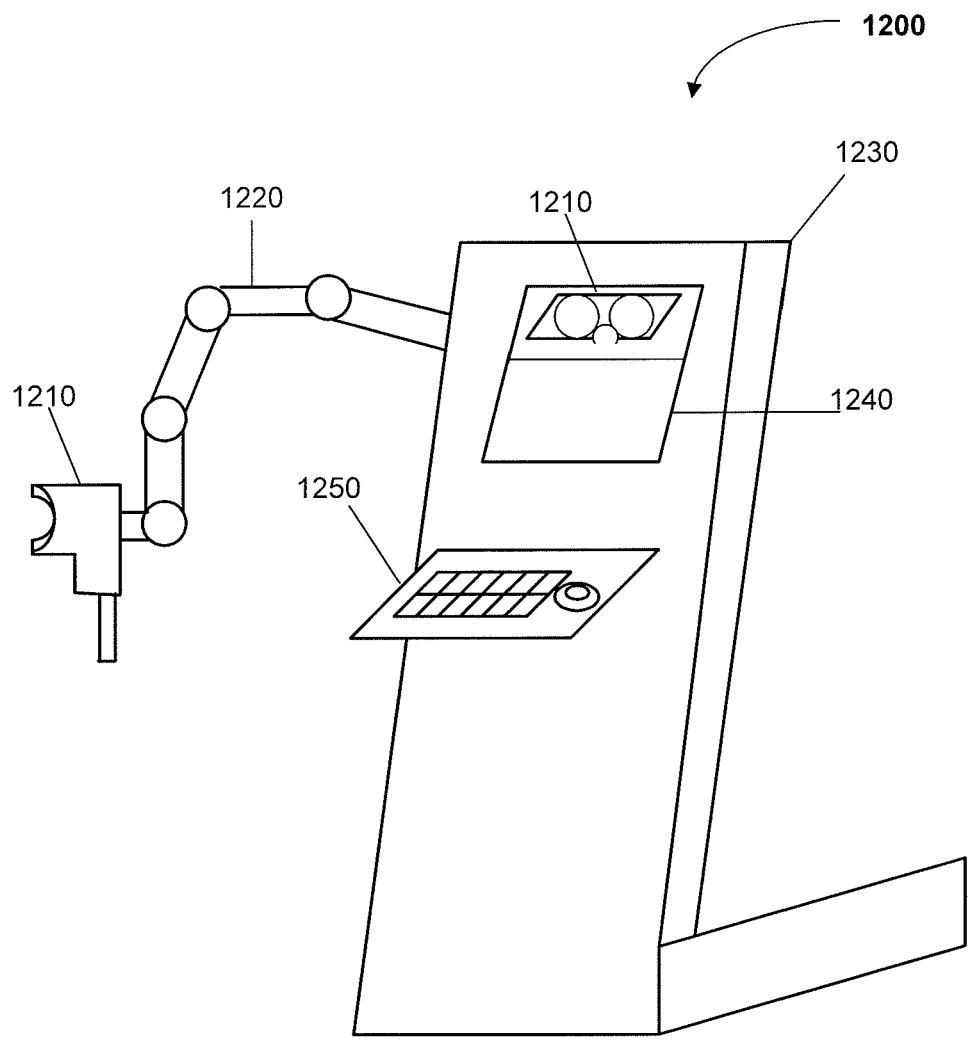
FIG. 12 depicts an example self-service kiosk according to an illustrative embodiment of the present invention.

FIG. 12 depicts an illustrative kiosk 1200 that may be used in implementing an illustrative embodiment of the present invention. In an embodiment of the current invention, kiosks 1200 utilizing the system described herein may be set-up in consumer/patient friendly locations such as a doctors offices, drugstores, grocery stores, malls, department of motor vehicle offices, etc. These kiosks 1200 may be considered standalone machines 900, 1000 or multiple machines coupled together as a network 1100.

An embodiment of a kiosk may consist of an upright stand 1230 designed to house all the required components (e.g., fundus imager 100, computer 900). Alternatively, the kiosk may be implemented in a sit-down booth style (not shown). Both styles may include a lens mask 1210 which may enable a fundus image 300 of a patient's retina to be taken. Also available are the standard equipment to better receive a fundus image such as, but not limited to, forehead support and chin rest (not shown). Lens mask 1210 may be available with an adjustable arm 1220 which may accommodate various patient heights. Kiosk may include an input device 1250 which may allow a patient to input data into the system. Data may include patient name, address, demographic information, history of illnesses, etc. Kiosk may also include a data output device such as a video screen 1240 (e.g., but not limited to, an LCD display). The video screen 1240 may provide, for example, an echo of the input from 1250, patient instructions and/or marketing material to the consumer.

The current invention is not limited to the specific embodiments of the invention illustrated herein by way of example, but is defined by the claims. One of ordinary skill in the art would recognize that various modifications and alternatives to the examples discussed herein are possible without departing from the scope and general concepts of this invention.

We claim:

1. A retinal abnormalities detection system, comprising:
a retinal scanner constructed to obtain retinal data;
a central processing unit (CPU) in communication with the retinal scanner, the CPU comprising memory-storable CPU-executable instructions for detecting retinal abnormalities;
wherein the CPU performs the following in response to receiving retinal data based on the memory-storable CPU-executable instructions:
a formation of a retinal image based on the retinal data;
an analysis of the retinal image, wherein the analysis comprises:
locating one or more edges at each level of a pyramid decomposition of the retinal image,
obtaining one or more binary mask images where the one or more edges are located,
calculating a final mask as a logical union of the one or more binary mask images,
creating a testing mask by morphologically closing the final mask, and
creating a training mask by taking a logical complement of a dilated final mask; and
a detection of an abnormality based on training an anomaly detector on the training mask and applying the anomaly detector on the testing mask.

2. The system according to claim 1, wherein the detection of an abnormality further comprises using an algorithm based on:
a machine learning single class classifier.

3. The system according to claim 1, wherein the detection of an abnormality further comprises using an algorithm based on:
a support vector data description (SVDD); a support vector machine (SVM); a relevance vector machine (RVM); a neural network; neural analysis; a large margin classifier; a kernel based classifier; a probability density function (PDF) estimator; a Parzen PDF estimator; a Bayesian classifier; a Constant False Alarm Rate (CFAR) detector; or a fuzzy logic based classifier.

4. The system according to claim 1, wherein the central processing unit is remotely located from the retinal scanner.

5. The system according to claim 1, wherein the central processing unit and the retinal scanner are integrated together in a kiosk.

6. The system according to claim 1, wherein the detection of an abnormality comprises detection of age related macular degeneration, macular and retinal degenerations, a diabetic retinopathy, a diabetic macular edema, a retinal vein occlusion, a vitreomacular interface abnormality, a macular hole, an epiretinal membrane, retinal vasculopathies, maculopathies, an optic nerve pathology, or glaucomatous optic nerve damage.

7. The system according to claim 1, wherein the analysis of the retinal image further comprises detecting and excluding a non-pathological anatomical feature from the retinal image.

8. The system according to claim 1, wherein the analysis of the retinal image further comprises:
detecting and excluding from the retinal image an optic disk region near an optic nerve, a non-pathological pigmentation, a lesion, or a blood vessel;
selecting from a parsed local region in order to identify anomalies; or
selecting from the parsed local region in order to exclude anomalies.

9. The system according to claim 1, wherein the analysis of the retinal image is limited to:
   a prescribed region of the retinal image; or
   a random selection of pixels from the retinal image.

10. The system according to claim 1, wherein the analysis of the retinal image further comprises:
   using full red, green, and blue (RGB) color components of the retinal image, extracting a green channel from the retinal image, extracting a red channel from the retinal image, extracting a blue channel from the retinal image, performing intensity remapping of the retinal image, performing contrast stretching of the retinal image, performing image enhancement, performing thresholding of the retinal image, performing image registration and matching, performing remapping of an original (RGB) color space into another color space, performing stochastic classification of pixels of the retinal image into different classes, performing best feature selection using principal component analysis (PCA) on the retinal image, segmenting retinal anatomical features in the retinal image, segmenting retinal vasculature in the retinal image, segmenting fovea in the retinal image, creating a feature vector, performing connected components on anomalous pixels of the retinal image to obtain anomalous blobs, performing intensity equalization on the retinal image, performing texture analysis of the retinal image, obtaining a wavelet signature of pixels of the retinal image, or performing multi-resolution processing of the retinal image.

11. The system according to claim 1, wherein the analysis of the retinal image further comprises:
   linear filtering, spectral filtering, nonlinear filtering, low pass filtering, median filtering, performing histogram equalization, performing adaptive histogram equalization, normalizing the retinal data, whitening the retinal data, performing band selection on the retinal data, performing dimensionality reduction on the retinal data, performing best feature and classifier selection using Boosting, computing a gradient, computing a Hessian, performing global static window analysis, performing local static window analysis, performing local sliding window analysis, comparing probability distribution functions (PDFs) of retinal data features using histograms, comparing PDFs of retinal data features using mutual information, comparing PDFs of retinal data features using correlation, comparing PDFs of retinal data features using Kullback-Leiber (KL) distance, using segmentation of the retinal data, creating a feature vector composed of original single band data, creating a feature vector composed of original multi band data, creating a feature vector composed by downselecting original multi band data, creating a feature vector composed of output from filtering original data, creating a feature vector composed of a wavelet analysis of original data, creating a feature vector composed of a statistical measure derived from a single or multiple bands of the retinal data, creating a feature vector composed of morphological features of the retinal data, creating a feature vector composed of shape features of anomalous blobs, creating a feature vector composed of an area of detected objects, using binary level mathematical morphological operations, using grey level mathematical morphological operations, using binary level mathematical morphological filters, using grey level mathematical morphological filters, or creating a feature vector.

12. The system according to claim 1, wherein the retinal data is acquired from a fundus imager, a non-mydriatic fundus imager, a mydriatic fundus imager, an optical coherent tomography system, a monochromatic imager, a portable optical coherence tomography machine, a multispectral camera, a hyperspectral sensor, a scanning laser ophthalmoscopy system, an eye fundus angiography system, a stereoscopic imaging system, or a multi-modality system.

13. The system according to claim 1, wherein the anomaly detector comprises:
   a global anomaly detector; or
   a local anomaly detector.

14. The system according to claim 1, wherein the one or more edges are located based on:
   color, gradient, texture, intensity derived features, depth, area, or shape derived features.

15. The system according to claim 1, further comprising:
   detecting a second abnormality based on a longitudinal study comprising:
      comparing the retinal image with a second retinal image and detecting the second abnormality in the retinal image based on:
      counting pixels; or
      change detection.

16. The system according to claim 1, wherein the detection of an abnormality comprises incorporation of: demographic information, age data, race data, ocular information, ph level, ocular pressure, arterovenous ratio, systemic factors, body mass index data, blood pressure data, genetic information, family history data, or a patient severity scale.

17. The system according to claim 1, wherein the detection of an abnormality further comprises:
   analyzing the retinal image for a quality criterion; and
   requesting new retinal data when the retinal image does not meet the quality criterion.

18. The system according to claim 17, wherein the quality criterion comprises: sharpness, focus, contrast, or presence of artifacts due to illumination.

19. A method for automated detection of retinal abnormalities, comprising:
   receiving retinal data of the retina of a subject from a retinal scanner, wherein the retinal scanner is in communication with a computer;
   forming, by the computer, a retinal image based on the retinal data;
   locating, by the computer, one or more edges at each level of a pyramid decomposition of the retinal image;
   obtaining, by the computer, one or more binary mask images where the one or more edges are located;
   calculating, by the computer, a final mask as a logical union of the one or more binary mask images;
   creating, by the computer, a testing mask by morphologically closing the final mask;
   creating, by the computer, a training mask by taking a logical complement of a dilated final mask; and
   determining an area of abnormality in the retinal image by training an anomaly detector on the training mask and applying the anomaly detector on the testing mask using the computer.

20. The method according to claim 19, wherein the determining an area of abnormality further comprises using an algorithm based on:
   a machine learning single class classifier.

21. The method according to claim 19, wherein the determining an area of abnormality further comprises using an algorithm based on:
   a support vector data description (SVDD), a support vector machine (SVM), a relevance vector machine (RVM), a neural network, neural analysis, a large margin classifier, a kernel based classifier, a probability density function (PDF) estimator, a Parzen PDF estimator, a Bayesian classifier, a Constant False Alarm Rate (CFAR) detector, or a fuzzy logic based classifier.

22. The method according to claim 19, wherein the determining an area of abnormality comprises detection of age related macular degeneration, macular and retinal degenerations, a diabetic retinopathy, a diabetic macular edema, a retinal vein occlusion, a vitreomacular interface abnormality, a macular hole, an epiretinal membrane, retinal vasculopathies, maculopathies, an optic nerve pathology, or glaucomatous optic nerve damage.

23. The method according to claim 19, further comprising detecting and excluding a non-pathological anatomical feature of the retinal image using the computer.

24. The method according to claim 19, further comprising:
    detecting and excluding from the retinal image an optic disk region near an optic nerve, a non-pathological pigmentation, a lesion, or a blood vessel using the computer;
    selecting from a parsed local region in order to identify anomalies using the computer; or
    selecting from the parsed local region in order to exclude anomalies using the computer.

25. The method according to claim 19, wherein the retinal image is limited to:
    a prescribed region of the retinal image; or
    a random selection of pixels from the retinal image.

26. The method according to claim 19, further comprising:
    using full red, green, and blue (RGB) color components of the retinal image, extracting a green channel from the retinal image, extracting a red channel from the retinal image, extracting a blue channel from the retinal image, performing intensity remapping of the retinal image, performing contrast stretching of the retinal image, performing image enhancement, performing thresholding of the retinal image, performing image registration and matching, performing remapping of an original (RGB) color space into another color space, performing stochastic classification of pixels of the retinal image into different classes, performing best feature selection using principal component analysis (PCA) on the retinal image, segmenting retinal anatomical features in the retinal image, segmenting retinal vasculature in the retinal image, segmenting fovea in the retinal image, creating a feature vector, performing connected components on anomalous pixels of the retinal image to obtain anomalous blobs, performing intensity equalization on the retinal image, performing texture analysis of the retinal image, obtaining a wavelet signature of pixels of the retinal image, or performing multi-resolution processing of the retinal image.

27. The method according to claim 19, further comprising:
    linear filtering, spectral filtering, nonlinear filtering, low pass filtering, median filtering, performing histogram equalization, performing adaptive histogram equalization, normalizing the retinal data, whitening the retinal data, performing band selection on the retinal data, performing dimensionality reduction on the retinal data, performing best feature and classifier selection using Boosting, computing a gradient, computing a Hessian, performing global static window analysis, performing local static window analysis, performing local sliding window analysis, comparing probability distribution functions (PDFs) of retinal data features using histograms, comparing PDFs of retinal data features using mutual information, comparing PDFs of retinal data features using correlation, comparing PDFs of retinal data features using Kullback-Leiber (KL) distance, using segmentation of the retinal data, creating a feature vector composed of original single band data, creating a feature vector composed of original multi band data, creating a feature vector composed by downselecting original multi band data, creating a feature vector composed of output from filtering original data, creating a feature vector composed of a wavelet analysis of original data, creating a feature vector composed of a statistical measure derived from a single or multiple bands of the retinal data, creating a feature vector composed of morphological features of the retinal data, creating a feature vector composed of shape features of anomalous blobs, creating a feature vector composed of an area of detected objects, using binary level mathematical morphological operations, using grey level mathematical morphological operations, using binary level mathematical morphological filters, using grey level mathematical morphological filters, or creating a feature vector.

28. The method according to claim 19, wherein the retinal data is acquired from a standard fundus imager, a non-mydriatic imager, a mydriatic fundus imager, an optical coherent tomography system, a monochromatic imager, a portable optical coherence tomography machine, a multispectral camera, a hyperspectral sensor, a scanning laser ophthalmoscopy system, an eye fundus angiography system, a stereoscopic imaging system, or a multi-modality system.

29. The method according to claim 19, wherein the anomaly detector comprises:
    a global anomaly detector; or
    a local anomaly detector.

30. The method according to claim 19, wherein the one or more edges are located based on:
    color, gradient, texture, intensity derived features, depth, area, or shape derived features.

31. The method according to claim 19, further comprising:
    detecting a second area of abnormality based on a longitudinal study comprising:
        comparing the retinal image with a second retinal image and detecting the second area of abnormality in the retinal image based on:
            counting pixels; or
            change detection.

32. The method according to claim 19, wherein the detection of an area of abnormality further comprises:
    incorporating demographic information, age data, race data, ocular information, ph level, ocular pressure, arterovenous ratio, systemic factors, body mass index data, blood pressure data, genetic information, family history data, or a patient severity scale using the computer.

33. A non-transitory computer-readable medium storing executable instructions for execution by a computer having memory, the medium storing instructions for to:
    receive retinal data from a retinal scanner coupled to the computer;
    form a retinal image based on the retinal data;
    locate one or more edges at each level of a pyramid decomposition of the retinal image;
    obtain one or more binary mask images where the one or more edges are located;
    calculate a final mask as a logical union of the one or more binary mask images;
    create a testing mask by morphologically closing the final mask;

create a training mask by taking a logical complement of a dilated final mask; and determine an area of abnormality in the retinal image by training an anomaly detector on the training mask and applying the anomaly detector on the testing mask.

34. The non-transitory computer-readable medium according to claim 33, wherein the determining an area of abnormality further comprises an algorithm based on:

a machine learning single class classifier.

35. The non-transitory computer-readable medium according to claim 33, wherein the determining an area of abnormality further comprises an algorithm based on:

a support vector data description (SVDD); a support vector machine (SVM); a relevance vector machine (RVM); a neural network; neural analysis; a large margin classifier; a kernel based classifier; a probability density function (PDF) estimator; a Parzen PDF estimator; a Bayesian classifier; a Constant False Alarm Rate (CFAR) detector; or a fuzzy logic based classifier.

36. The non-transitory computer-readable medium according to claim 33, wherein the determining an area of abnormality comprises detection of age related macular degeneration, macular and retinal degenerations, a diabetic retinopathy, a diabetic macular edema, a retinal vein occlusion, a vitreomacular interface abnormality, a macular hole, an epiretinal membrane, retinal vasculopathies, maculopathies, an optic nerve pathology, or glaucomatous optic nerve damage.

37. The non-transitory computer-readable medium according to claim 33, further comprising instructions to:

detect and exclude a non-pathological anatomical feature from the retinal image.

38. The non-transitory computer-readable medium according to claim 33, further comprising instructions to:

detect and exclude from the retinal image an optic disk region near an optic nerve, a non-pathological pigmentation, a lesion, or a blood vessel;

select from a parsed local region in order to identify anomalies; or select from the parsed local region in order to exclude anomalies.

39. The non-transitory computer-readable medium according to claim 33, wherein the retinal image is limited to:

a prescribed region of the retinal image; or a random selection of pixels from the retinal image.

40. The non-transitory computer-readable medium according to claim 33, further comprising instructions to:

use full red, green, and blue (RGB) color components of the retinal image, extract a green channel from the retinal image, extract a red channel from the retinal image, extract a blue channel from the retinal image, perform intensity remapping of the retinal image, perform contrast stretching of the retinal image, perform image enhancement, perform thresholding of the retinal image, perform image registration and matching, perform remapping of an original (RGB) color space into another color space, perform stochastic classification of pixels of the retinal image into different classes, perform best feature selection using principal component analysis (PCA) on the retinal image, segment retinal anatomical features in the retinal image, segment retinal vasculature in the retinal image, segment fovea in the retinal image, create a feature vector, perform connected components on anomalous pixels of the retinal image to obtain anomalous blobs, perform intensity equalization on the retinal image, perform texture analysis of the retinal image, obtain a wavelet signature of pixels of the retinal image, or perform multi-resolution processing of the retinal image.

41. The non-transitory computer-readable medium according to claim 33, further comprising instructions to:

perform linear filtering, perform spectral filtering, perform nonlinear filtering, perform low pass filtering, perform median filtering, perform histogram equalization, perform adaptive histogram equalization, normalize the retinal data, whiten the retinal data, perform band selection on the retinal data, perform dimensionality reduction on the retinal data, perform best feature and classifier selection using Boosting, compute a gradient, compute a Hessian, perform global static window analysis, perform local static window analysis, perform local sliding window analysis, compare probability distribution functions (PDFs) of retinal data features using histograms, compare PDFs of retinal data features using mutual information, compare PDFs of retinal data features using correlation, compare PDFs of retinal data features using Kullback-Leiber (KL) distance, use segmentation of the retinal data, create a feature vector composed of original single band data, create a feature vector composed of original multi band data, create a feature vector composed by downselecting original multi band data, create a feature vector composed of output from filtering original data, create a feature vector composed of a wavelet analysis of original data, create a feature vector composed of a statistical measure derived from a single or multiple bands of the retinal data, create a feature vector composed of morphological features of the retinal data, create a feature vector composed of shape features of anomalous blobs, create a feature vector composed of an area of detected objects, use binary level mathematical morphological operations, use grey level mathematical morphological operations, use binary level mathematical morphological filters, use grey level mathematical morphological filters, or create a feature vector.

42. The non-transitory computer-readable medium according to claim 33, wherein the retinal data is acquired from a fundus imager; a non-mydriatic imager; a mydriatic fundus imager; an optical coherent tomography system, a monochromatic imager, a portable optical coherence tomography machine, a multispectral camera, a hyperspectral sensor, a scanning laser ophthalmoscopy system, an eye fundus angiography system, a stereoscopic imaging system, or a multi-modality system.

43. The non-transitory computer-readable medium according to claim 33, wherein the anomaly detector comprises:

a global anomaly detector; or a local anomaly detector.

44. The non-transitory computer-readable medium according to claim 33, wherein the one or more edges are located based on:

color, gradient, texture, intensity derived features, depth, area, or shape derived features.

45. The non-transitory computer-readable medium according to claim 33, further comprising:

detecting a second area of abnormality based on a longitudinal study comprising:

comparing the retinal image with a second retinal image and detecting the second area of abnormality in the retinal image based on:

counting pixels; or change detection.

46. The non-transitory computer-readable medium according to claim 33, wherein the detection of the area of abnormality further comprises instructions to incorporate demographic information, age data, race data, ocular information, ph level, ocular pressure, arterovenous ratio, systemic factors, body mass index data, blood pressure data, genetic information, family history data, or a patient severity scale.

47. The non-transitory computer-readable medium according to claim 33, wherein the determining an area of abnormality further comprises:
   analyzing the retinal image for a quality criterion; and
   requesting new retinal data when the retinal image does not meet the quality criterion.

48. The non-transitory computer-readable medium according to claim 47, wherein the quality criterion comprises: sharpness, focus, contrast, or presence of artifacts due to illumination.

* * * * *